(12) United States Patent
Soucaille et al.

(10) Patent No.: US 9,051,588 B2
(45) Date of Patent: Jun. 9, 2015

(54) MICROORGANISMS AND METHODS FOR PRODUCTION OF 1,2-PROPANEDIOL AND ACETOL

(75) Inventors: Philippe Soucaille, Deyme (FR); Isabelle Meynial Salles, Fourquevaux (FR); François Voelker, Montrond les Bains (FR); Rainer Figge, Le Crest (FR)

(73) Assignee: METABOLIC EXPLORER, Saint Beauzire (FR)

( * ) Notice: Subject to any disclaimer, the term of this patent is extended or adjusted under 35 U.S.C. 154(b) by 673 days.

(21) Appl. No.: 12/532,469

(22) PCT Filed: Mar. 21, 2008

(86) PCT No.: PCT/EP2008/053448
§ 371 (c)(1),
(2), (4) Date: Sep. 22, 2009

(87) PCT Pub. No.: WO2008/116853
PCT Pub. Date: Oct. 2, 2008

(65) Prior Publication Data
US 2011/0201070 A1 Aug. 18, 2011

(30) Foreign Application Priority Data
Mar. 23, 2007 (WO) ............... PCT/IB2007/001677

(51) Int. Cl.
| | |
|---|---|
| *C12N 1/20* | (2006.01) |
| *C12N 9/88* | (2006.01) |
| *C12N 9/02* | (2006.01) |
| *C12N 15/00* | (2006.01) |
| *C12P 7/18* | (2006.01) |
| *C07H 21/04* | (2006.01) |
| *C12N 15/70* | (2006.01) |
| *C12N 9/04* | (2006.01) |
| *C12P 7/26* | (2006.01) |

(52) U.S. Cl.
CPC . *C12P 7/18* (2013.01); *C12N 15/70* (2013.01); *C12N 9/0006* (2013.01); *C12N 9/88* (2013.01); *C12N 9/0004* (2013.01); *C12P 7/26* (2013.01)

(58) Field of Classification Search
CPC ........ C12N 9/88; C12N 9/0006; C12N 15/70; C12P 7/18
See application file for complete search history.

(56) References Cited

U.S. PATENT DOCUMENTS

| 6,087,140 A | 7/2000 | Cameron et al. |
|---|---|---|
| 6,303,352 B1 | 10/2001 | Cameron et al. |
| 2004/0152174 A1* | 8/2004 | Cervin et al. ............... 435/106 |
| 2005/0054060 A1 | 3/2005 | Chateau et al. |
| 2007/0072279 A1 | 3/2007 | Meynial-Salles et al. |
| 2009/0186392 A1 | 7/2009 | Gonzalez |

FOREIGN PATENT DOCUMENTS

| CN | 1860221 | 11/2006 |
|---|---|---|
| CN | 1910278 | 2/2007 |
| DE | 41 28 692 A1 | 3/1993 |
| WO | 98/37204 | 8/1998 |
| WO | 2004/033646 A2 | 4/2004 |
| WO | 2005/095536 A2 | 10/2005 |

OTHER PUBLICATIONS

Ferguson et al., "Methylglyoxal production in bacteria: suicide or survival?," Arch Microbiol (1998), 170, pp. 209-219.
Grant, Anne W. et al., "A novel aldo-keto reductase from *Escherichia coli* can increase resistance to methylglyoxal toxicity." FEMS Microbiology Letters, vol. 218, No. 1, Jan. 21, 2003, pp. 93-99, XP002455919, ISSN: 0378-1097.
Bennett, G. N. et al., "Microbial formation, biotechnological production and applications of 1, 2-propanediol", Applied Microbiology and Biotechnology, vol. 55, No. 1, Jan. 2001, pp. 1-9, XP002455920, ISSN: 0175-7598.
Ko, Junsang et al., "Conversion of methylglyoxal to acetol by *Escherichia coli* aldo-keto Reductases", Journal of Bacteriology, vol. 187, No. 16, Aug. 2005, pp. 5782-5789, XP002455921, ISSN: 0021-9193.
Misra, Kanika et al., "Reduction of methylglyoxal in *Escherichia coli* K-12 by an aldehyde reductase and alcohol dehydrogenase" Molecular and Cellular Biochemistry, vol. 156, No. 2, 1996, pp. 117-124, ISSN: 0300-8177.
Altaras, N. E., et al., "Enhanced production of (R)-1, 2-propanediol by metabolically engineered *Escherichia coli*", Biotechnology Progress, XX, XX, vol. 16, No. 6, Nov. 2000, pp. 940-946, XP002293971, ISSN: 8756-7938.
Altaras, N. E., et al., "Metabolic engineering of a 1, 2-Propanediol pathway in *Escherichia coli*", Applied and Environmental Microbiology, Wahsington, DC, US, vol. 65, No. 3, Mar. 1999, pp. 1180-1185, XP02293970, ISSN: 0099-2240.
International Search Report for PCT/EP2008/053448 dated Jun. 25, 2008 (4 pages).
Badia et al., "Fermentation Mechanism of Fucose and Rhamnose in *Salmonella typhimurium* and *Klebsiella pneumoniae*," Journal of Bacteriology, Jan. 1985, pp. 435-437.
Tran-Din et al., "Formation of D(-)-1,2-propanediol and D9-)-lactate from glucose by *Clostridium* sphenoides under phosphate limitation," Arch Microbiol (1985), 142:87-92.
Cameron et al., "A Novel Fermentation: The Production of R(-)-1,2-Propanediol and Acetol by *Clostridium thermosaccharolyticum*," Bio/Technology, Jul. 1986, vol. 4, pp. 651-654.
Sanchez-Riera et al., "Influence of Environmental Factors in the Production of R(-)-1,2-Propanediol by *Clostridium thermosaccharolyticum*," Biotechnology Letters (1987), vol. 9, No. 7, pp. 449-454.

(Continued)

*Primary Examiner* — Yong Pak
(74) *Attorney, Agent, or Firm* — Miles & Stockbridge P.C.

(57) ABSTRACT

The present invention concerns a modified microorganism with an increased methylglyoxal reductase activity, and its use for the preparation of 1,2-propanediol and/or acetol. In particular this increased methylglyoxal reductase activity is obtained by increasing the expression of specific genes from microorganisms.
This invention is also related to a method for producing 1,2-propanediol and/or acetol by fermentation of a microorganism having an increased methylglyoxal reductase activity.

31 Claims, 2 Drawing Sheets

(56) References Cited

OTHER PUBLICATIONS

Cooper, "Metabolism of Methylglyoxal in Microorganisms," Ann. Rev. Microbiol. 1984, 38:49-68.

Totemeyer et al., "From famine to feast: the role of methylglyoxal production in *Escherichia coli*," Molecular Microbiology (1998), 27(3), pp. 553-562.

Saikusa et al., "Metabolism of 2-Oxoaldehydes in Bacteria: Purification and Characterization of Methylglyoxal Reductase from *Escherichia coli*," Agric. Biol. Chem., 51(7), 1987, pp. 1893-1899.

Misra et al., "Reduction of methylglyoxal in *Escherichia coli* K12 by an aldehyde reductase and alcohol dehydrogenase," Molecular and Cellular biochemistry, 1996, 156:117-124.

Altaras et al., "Metabolic Engineering of a 1,2-Propanediol Pathway in *Escherichia coli*," Applied and Environmental Microbiology, Mar. 1999, pp. 1180-1185.

Grant et al., "A novel aldo-keto reductase from *Escherichia coli* can increase resistance to methylglyoxal toxicity," FEMS Microbiology Letters, 2003, 218, pp. 93-99.

Di Luccio et al., "Identification of a novel NADH-specific aldo-keto reductase using sequence and structural homologies," Biochem. J. (2006) 400, pp. 105-114.

Ko et al., "Conversion of Methylglyoxal to Acetol by *Escherichia coli* Aldo-Keto Reductases," Journal of Bacteriology, Aug. 2005, pp. 5782-5789.

Cameron et al., "Metabolic Engineering of Propanediol Pathways," Biotechnol. Prog. 1998, 14, pp. 116-125.

Huang et al., "Characterization of Methylglyoxal Synthase from *Clostridium acetobutylicum* ATCC 824 and Its Use in the Formation of 1,2-Propanediol," Applied and Environmental Microbiology, Jul. 1999, pp. 3244-3247.

Berrios-Rivera et al., "The effect of carbon sources and lactate dehydrogenase deletion on 1,2-propanediol production in *Escherichia coli*," J. Ind. Microbiol. Biotechnol. 2003, 30:34-40.

Datsenko et al., "One-step inactivation of chromosomal genes in *Escherichia coli* K-12 using PCR products," PNAS, Jun. 6, 2000, vol. 97, No. 12, pp. 6640-6645.

Anderson, "Growth Requirements of Virus-Resistant Mutants of *Escherichia coli* Strain "B"," Proc. N.A.S., Mar. 21, 1946, pp. 120-128.

Schaefer et al., "Automated Sampling Device for Monitoring Intracellular Metabolite Dynamics," Analytical Biochemistry (1999), 270, pp. 88-96.

Wiesenborn et al., "Thiolase from *Clostridium acetobutylicum* ATCC 824 and Its Role in the Synthesis of Acids and Solvents," Applied and Environmental Microbiology, Nov. 1988, pp. 2717-2722.

Monot et al., "Acetone and Butanol Production by *Clostridium acetobutylicum* in a Synthetic Medium," Applied and Environmental Microbiology, Dec. 1982, pp. 1318-1324.

Vasconcelos et al., "Regulation of Carbon and Electron Flow in *Clostridium acetobutylicum* Grown in Chemostat Culture at Neutral pH on Mixtures of Glucose and Glycerol," Journal of Bacteriology, Mar. 1994, pp. 1443-1450.

Oh et al "Global Expression Profiling of Acetate-Grown *Escherichia Coli*", JBC Papers in Press. Published Jan. 28, 2002, p. 1 & 13.

\* cited by examiner

SEQUENCE LISTING

<160> NUMBER OF SEQ ID NOS: 73

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
ggtgatgata gttatcgccg          20

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
cgtgccatcg acagcagtcc          20

<210> SEQ ID NO 3
<211> LENGTH: 30
<212> TYPE: DNA
<213> ORGANISM: Artificial Sequence
<220> FEATURE:
<223> OTHER INFORMATION: PCR primer

<400> SEQUENCE: 3
agacattaaa aatatacgtg cagctacccg          30

<210> SEQ ID NO 4
<211> LENGTH: 30
<212> TYPE: DNA

```
<213> ORGANISM: Artificial Sequence
<220> FEATURE:
<223> OTHER INFORMATION: PCR primer

<400> SEQUENCE: 4
gtgaaagctg acaaccfttt tgatctttta                                          30

<210> SEQ ID NO 5
<211> LENGTH: 22
<212> TYPE: DNA
<213> ORGANISM: Artificial Sequence
<220> FEATURE:
<223> OTHER INFORMATION: PCR primer

<400> SEQUENCE: 5
ggctcattgc accaccatcc ag                                                  22

<210> SEQ ID NO 6
<211> LENGTH: 24
<212> TYPE: DNA
<213> ORGANISM: Artificial Sequence
<220> FEATURE:
<223> OTHER INFORMATION: PCR primer

<400> SEQUENCE: 6
gaaaagacgc gctgacaata cgcc                                                24

<210> SEQ ID NO 7
<211> LENGTH: 20
<212> TYPE: DNA
<213> ORGANISM: Artificial Sequence
<220> FEATURE:
<223> OTHER INFORMATION: PCR primer

<400> SEQUENCE: 7
gccatcagca ggcttagccg                                                     20

<210> SEQ ID NO 8
<211> LENGTH: 23
<212> TYPE: DNA
<213> ORGANISM: Artificial Sequence
<220> FEATURE:
<223> OTHER INFORMATION: PCR primer

<400> SEQUENCE: 8
gggtattgtg gcatgtttaa ccg                                                 23

<210> SEQ ID NO 9
<211> LENGTH: 31
<212> TYPE: DNA
<213> ORGANISM: Artificial Sequence
<220> FEATURE:
<223> OTHER INFORMATION: PCR primer

<400> SEQUENCE: 9
gaagtggtcg atgccgggat tgaagaatgg g                                        31

<210> SEQ ID NO 10
<211> LENGTH: 31
<212> TYPE: DNA
<213> ORGANISM: Artificial Sequence
<220> FEATURE:
<223> OTHER INFORMATION: PCR primer

<400> SEQUENCE: 10
gggttacgtt tcagtgaggc gcgttctgcg g                                        31
```

```
<210> SEQ ID NO 11
<211> LENGTH: 31
<212> TYPE: DNA
<213> ORGANISM: Artificial Sequence
<220> FEATURE:
<223> OTHER INFORMATION: PCR primer

<400> SEQUENCE: 11
tgcagcggcg cacgatggcg acgttccgcc g                              31

<210> SEQ ID NO 12
<211> LENGTH: 31
<212> TYPE: DNA
<213> ORGANISM: Artificial Sequence
<220> FEATURE:
<223> OTHER INFORMATION: PCR primer

<400> SEQUENCE: 12
cacgatgacg accattcatg cctatactgg c                              31

<210> SEQ ID NO 13
<211> LENGTH: 40
<212> TYPE: DNA
<213> ORGANISM: Artificial Sequence
<220> FEATURE:
<223> OTHER INFORMATION: PCR primer

<400> SEQUENCE: 13
catatttccc tcaaagaata taaaaaagaa caattaacgc                     40

<210> SEQ ID NO 14
<211> LENGTH: 31
<212> TYPE: DNA
<213> ORGANISM: Artificial Sequence
<220> FEATURE:
<223> OTHER INFORMATION: PCR primer

<400> SEQUENCE: 14
tatgttcatg cgatggcgca ccagctgggc g                              31

<210> SEQ ID NO 15
<211> LENGTH: 24
<212> TYPE: DNA
<213> ORGANISM: Artificial Sequence
<220> FEATURE:
<223> OTHER INFORMATION: PCR primer

<400> SEQUENCE: 15
ccccggaatc agaggaatag tccc                                      24

<210> SEQ ID NO 16
<211> LENGTH: 29
<212> TYPE: DNA
<213> ORGANISM: Artificial Sequence
<220> FEATURE:
<223> OTHER INFORMATION: PCR primer

<400> SEQUENCE: 16
gggtagactc cattactgag gcgtgggcg                                 29

<210> SEQ ID NO 17
<211> LENGTH: 20
<212> TYPE: DNA
<213> ORGANISM: Artificial Sequence
<220> FEATURE:
```

<223> OTHER INFORMATION: Specific primer

<400> SEQUENCE: 17
gccatcagca ggcttagcgc                                              20

<210> SEQ ID NO 18
<211> LENGTH: 23
<212> TYPE: DNA
<213> ORGANISM: Artificial Sequence
<220> FEATURE:
<223> OTHER INFORMATION: Specific primer

<400> SEQUENCE: 18
gggtattgtg gcatgtttaa ccg                                          23

<210> SEQ ID NO 19
<211> LENGTH: 33
<212> TYPE: DNA
<213> ORGANISM: Artificial Sequence
<220> FEATURE:
<223> OTHER INFORMATION: Specific primer

<400> SEQUENCE: 19
ggcgtctcgc catacaacaa acgcacatcg ggc                               33

<210> SEQ ID NO 20
<211> LENGTH: 29
<212> TYPE: DNA
<213> ORGANISM: Artificial Sequence
<220> FEATURE:
<223> OTHER INFORMATION: Specific primer

<400> SEQUENCE: 20
gggctttgcc gacaccttct tcgttcttg                                    29

<210> SEQ ID NO 21
<211> LENGTH: 20
<212> TYPE: DNA
<213> ORGANISM: Artificial Sequence
<220> FEATURE:
<223> OTHER INFORMATION: Specific primer

<400> SEQUENCE: 21
cctgacccca tgccgaactc                                              20

<210> SEQ ID NO 22
<211> LENGTH: 21
<212> TYPE: DNA
<213> ORGANISM: Artificial Sequence
<220> FEATURE:
<223> OTHER INFORMATION: Specific primer

<400> SEQUENCE: 22
cccgcttccc tcaatacctg g                                            21

<210> SEQ ID NO 23
<211> LENGTH: 30
<212> TYPE: DNA
<213> ORGANISM: Artificial Sequence
<220> FEATURE:
<223> OTHER INFORMATION: Specific primer

<400> SEQUENCE: 23
gtggatcaag atgcccgcct gcggattccg                                   30

<210> SEQ ID NO 24
<211> LENGTH: 31
<212> TYPE: DNA
<213> ORGANISM: Artificial Sequence
<220> FEATURE:
<223> OTHER INFORMATION: Specific primer

<400> SEQUENCE: 24
cccgtccaga gcccgtgccg gggaatttgc c                          31

<210> SEQ ID NO 25
<211> LENGTH: 20
<212> TYPE: DNA
<213> ORGANISM: Artificial Sequence
<220> FEATURE:
<223> OTHER INFORMATION: Specific primer

<400> SEQUENCE: 25
ggcggtgagg gggggattcg                                       20

<210> SEQ ID NO 26
<211> LENGTH: 21
<212> TYPE: DNA
<213> ORGANISM: Artificial Sequence
<220> FEATURE:
<223> OTHER INFORMATION: Specific primer

<400> SEQUENCE: 26
ccccatcaac cactcgcggc c                                     21

<210> SEQ ID NO 27
<211> LENGTH: 29
<212> TYPE: DNA
<213> ORGANISM: Artificial Sequence
<220> FEATURE:
<223> OTHER INFORMATION: Specific primer

<400> SEQUENCE: 27
gccacagccg gaatcatact tggtttggg                             29

<210> SEQ ID NO 28
<211> LENGTH: 29
<212> TYPE: DNA
<213> ORGANISM: Artificial Sequence
<220> FEATURE:
<223> OTHER INFORMATION: Specific primer

<400> SEQUENCE: 28
cgtcaacacc aacttcgtcc catttcagg                             29

<210> SEQ ID NO 29
<211> LENGTH: 29
<212> TYPE: DNA
<213> ORGANISM: Artificial Sequence
<220> FEATURE:
<223> OTHER INFORMATION: PCR primer

<400> SEQUENCE: 29
gggtagactc cattactgag gcgtgggcg                             29

<210> SEQ ID NO 30
<211> LENGTH: 24
<212> TYPE: DNA
<213> ORGANISM: Artificial Sequence
<220> FEATURE:
<223> OTHER INFORMATION: PCR primer

<400> SEQUENCE: 30
ccacatgata ccgggatggt gacg					24

<210> SEQ ID NO 31
<211> LENGTH: 23
<212> TYPE: DNA
<213> ORGANISM: Artificial Sequence
<220> FEATURE:
<223> OTHER INFORMATION: PCR primer

<400> SEQUENCE: 31
ggcaattacc ctcgacgtac cgg					23

<210> SEQ ID NO 32
<211> LENGTH: 25
<212> TYPE: DNA
<213> ORGANISM: Artificial Sequence
<220> FEATURE:
<223> OTHER INFORMATION: PCR primer

<400> SEQUENCE: 32
ccgatggatg atctgttaga ggcgg					25

<210> SEQ ID NO 33
<211> LENGTH: 23
<212> TYPE: DNA
<213> ORGANISM: Artificial Sequence
<220> FEATURE:
<223> OTHER INFORMATION: PCR primer

<400> SEQUENCE: 33
ggcaattacc ctcgacgtac cgg					23

<210> SEQ ID NO 34
<211> LENGTH: 25
<212> TYPE: DNA
<213> ORGANISM: Artificial Sequence
<220> FEATURE:
<223> OTHER INFORMATION: PCR primer

<400> SEQUENCE: 34
ccgcctctaa cagatcatcc atcgg					25

<210> SEQ ID NO 35
<211> LENGTH: 100
<212> TYPE: DNA
<213> ORGANISM: Artificial Sequence
<220> FEATURE:
<223> OTHER INFORMATION: Specific primer

<400> SEQUENCE: 35
gaaactcgcc gtttatagca caaaacagta cgacaagaag tacctgcaac aggtgaacga		60 gtcctttggc tttgagctgg tgtaggctgg agctgcttcg					100

<210> SEQ ID NO 36
<211> LENGTH: 101
<212> TYPE: DNA
<213> ORGANISM: Artificial Sequence
<220> FEATURE:
<223> OTHER INFORMATION: Specific primer

<400> SEQUENCE: 36
ttaaaccagt tcgttcgggc aggtttcgcc tttttccaga ttgcttaagt tttgcagcgt		60 agtctgagaa atactggtca gcatatgaat atcctcctta g					101

<210> SEQ ID NO 37
<211> LENGTH: 100
<212> TYPE: DNA
<213> ORGANISM: Artificial Sequence
<220> FEATURE:
<223> OTHER INFORMATION: Specific primer

<400> SEQUENCE: 37
atgaacaact ttaatctgca caccccaacc cgcattctgt ttggtaaagg cgcaatcgct    60
ggtttacgcg aacaaattcc tgtaggctgg agctgcttcg                        100

<210> SEQ ID NO 38
<211> LENGTH: 101
<212> TYPE: DNA
<213> ORGANISM: Artificial Sequence
<220> FEATURE:
<223> OTHER INFORMATION: Specific primer

<400> SEQUENCE: 38
ttagcgggcg gcttcgtata tacggcggct gacatccaac gtaatgtcat gattttcgcc    60
cagttgggtc atgccgtgct ccatatgaat atcctcctta g                       101

<210> SEQ ID NO 39
<211> LENGTH: 99
<212> TYPE: DNA
<213> ORGANISM: Artificial Sequence
<220> FEATURE:
<223> OTHER INFORMATION: Specific primer

<400> SEQUENCE: 39
atggctatcc ctgcatttgg tttaggtact ttccgtctga aagacgacgt tgttatttca    60
tctgtgataa cggcgcttgt gtaggctgga gctgcttcg                          99

<210> SEQ ID NO 40
<211> LENGTH: 100
<212> TYPE: DNA
<213> ORGANISM: Artificial Sequence
<220> FEATURE:
<223> OTHER INFORMATION: Specific primer

<400> SEQUENCE: 40
tcccattcag gagccagacc ttccgggcta accaggcggt cgttgcaatc cagtgcggcg    60
atcgcttttt tatcttcggc catatgaata tcctccttag                        100

<210> SEQ ID NO 41
<211> LENGTH: 101
<212> TYPE: DNA
<213> ORGANISM: Artificial Sequence
<220> FEATURE:
<223> OTHER INFORMATION: Specific primer

<400> SEQUENCE: 41
ttacggtacg tcgtacccca gtgccgcttt acggatacga aaccattgtt gacgggtcat    60
tttcagtgtt tctgcttcga ctgtaggctg gagctgcttc g                       101

<210> SEQ ID NO 42
<211> LENGTH: 101
<212> TYPE: DNA
<213> ORGANISM: Artificial Sequence
<220> FEATURE:
<223> OTHER INFORMATION: Specific primer

```
<400> SEQUENCE: 42
atggttcagc gtattactat tgcgccgcaa ggcccggagt tttcccgttt tgtgatgggc    60
tactggcgat tgatggactg gcatatgaat atcctcctta g                      101

<210> SEQ ID NO 43
<211> LENGTH: 101
<212> TYPE: DNA
<213> ORGANISM: Artificial Sequence
<220> FEATURE:
<223> OTHER INFORMATION: Specific primer

<400> SEQUENCE: 43
atgagaataa atttcgcaca acgcttttcg ggagtcagta tggatatcat cttttatcac    60
ccaacgttcg atacccaatg gtgtaggctg gagctgcttc g                      101

<210> SEQ ID NO 44
<211> LENGTH: 99
<212> TYPE: DNA
<213> ORGANISM: Artificial Sequence
<220> FEATURE:
<223> OTHER INFORMATION: Specific primer

<400> SEQUENCE: 44
ttagtagccg cgtgcgcggt cgacttgccc gcagaccctc tcccctttt cgagctgggc    60 aatggtgcga gaaatgtacc atatgaatat cctccttag                          99

<210> SEQ ID NO 45
<211> LENGTH: 100
<212> TYPE: DNA
<213> ORGANISM: Artificial Sequence
<220> FEATURE:
<223> OTHER INFORMATION: Specific primer

<400> SEQUENCE: 45
agtcatatat tccaccagct atttgttagt gaataaaagc cacacattat tcgagccgga    60
tgattaatag tcaacagctc tgtaggctgg agctgcttcg                        100

<210> SEQ ID NO 46
<211> LENGTH: 79
<212> TYPE: DNA
<213> ORGANISM: Artificial Sequence
<220> FEATURE:
<223> OTHER INFORMATION: Specific primer

<400> SEQUENCE: 46
gctcacatta cgtgactgat tctaacaaaa cattaacacc aactggcaaa attttgtccc    60
atatgaatat cctccttag                                                79

<210> SEQ ID NO 47
<211> LENGTH: 102
<212> TYPE: DNA
<213> ORGANISM: Artificial Sequence
<220> FEATURE:
<223> OTHER INFORMATION: PCR primer

<400> SEQUENCE: 47
cgcgcgagac tcgctctgct tatctcgccc ggatagaaca agcgaaaact tcgaccgttc    60
atcgttcgca gttggcatgc ggtgtaggct ggagctgctt cg                     102

<210> SEQ ID NO 48
<211> LENGTH: 100
```

<212> TYPE: DNA
<213> ORGANISM: Artificial Sequence
<220> FEATURE:
<223> OTHER INFORMATION: PCR primer

<400> SEQUENCE: 48
gcttagcgcc ttctacagct tcacgcgcca gcttagtaat gcggtcgtaa tcgcccgctt    60
ccagcgcatc tgccggaacc catatgaata tcctccttag                         100

<210> SEQ ID NO 49
<211> LENGTH: 101
<212> TYPE: DNA
<213> ORGANISM: Artificial Sequence
<220> FEATURE:
<223> OTHER INFORMATION: Specific primer

<400> SEQUENCE: 49
atgcgtcttc ttcataccat gctgcgcgtt ggcgatttgc aacgctccat cgattttat    60 accaaagtgc tgggcatgaa gtgtaggctg gagctgcttc g                      101

<210> SEQ ID NO 50
<211> LENGTH: 100
<212> TYPE: DNA
<213> ORGANISM: Artificial Sequence
<220> FEATURE:
<223> OTHER INFORMATION: Specific primer

<400> SEQUENCE: 50
ttagttgccc agaccgcgac cggcgtcttt ctcttcgatt aactcaattt tgtaaccgtc    60
cggatcttcc acaaacgcga catatgaata tcctccttag                         100

<210> SEQ ID NO 51
<211> LENGTH: 101
<212> TYPE: DNA
<213> ORGANISM: Artificial Sequence
<220> FEATURE:
<223> OTHER INFORMATION: PCR primer

<400> SEQUENCE: 51
cgcggcgggt gccaacgttg tacgtatgaa cttttctcac ggctcgcctg aagatcacaa    60
aatgcgcgcg gataaagttc gtgtaggctg gagctgcttc g                      101

<210> SEQ ID NO 52
<211> LENGTH: 101
<212> TYPE: DNA
<213> ORGANISM: Artificial Sequence
<220> FEATURE:
<223> OTHER INFORMATION: PCR primer

<400> SEQUENCE: 52
cgccgcatcc ggcaacgtac ttactctacc gttaaaatac gcgtggtatt agtagaaccc    60
acggtactca tcacgtcgcc ccatatgaat atcctcctta g                      101

<210> SEQ ID NO 53
<211> LENGTH: 101
<212> TYPE: DNA
<213> ORGANISM: Artificial Sequence
<220> FEATURE:
<223> OTHER INFORMATION: PCR primer

<400> SEQUENCE: 53
cgcggcgggt gccaacgttg tacgtatgaa cttttctcac ggctcgcctg aagatcacaa    60
aatgcgcgcg gataaagttc gtgtaggctg gagctgcttc g                               101

<210> SEQ ID NO 54
<211> LENGTH: 101
<212> TYPE: DNA
<213> ORGANISM: Artificial Sequence
<220> FEATURE:
<223> OTHER INFORMATION: PCR primer

<400> SEQUENCE: 54
cgccgcatcc ggcaacgtac ttactctacc gttaaaatac gcgtggtatt agtagaaccc          60
acggtactca tcacgtcgcc ccatatgaat atcctcctta g                              101

<210> SEQ ID NO 55
<211> LENGTH: 24
<212> TYPE: DNA
<213> ORGANISM: Artificial Sequence
<220> FEATURE:
<223> OTHER INFORMATION: Specific primer

<400> SEQUENCE: 55
ccgacagtaa gacgggtaag cctg                                                 24

<210> SEQ ID NO 56
<211> LENGTH: 22
<212> TYPE: DNA
<213> ORGANISM: Artificial Sequence
<220> FEATURE:
<223> OTHER INFORMATION: Specific primer

<400> SEQUENCE: 56
agcttagtaa agccctcgct ag                                                   22

<210> SEQ ID NO 57
<211> LENGTH: 100
<212> TYPE: DNA
<213> ORGANISM: Artificial Sequence
<220> FEATURE:
<223> OTHER INFORMATION: Specific primer

<400> SEQUENCE: 57
catgggctag ctacgtatta attaaagatc tcctagggag ctcaccggtt aaaaataaga          60
gttaccttaa atggtaactc ttatttttt aggcgcgcca                                 100

<210> SEQ ID NO 58
<211> LENGTH: 100
<212> TYPE: DNA
<213> ORGANISM: Artificial Sequence
<220> FEATURE:
<223> OTHER INFORMATION: Specific primer

<400> SEQUENCE: 58
agcttggcgc gcctaaaaaa ataagagtta ccatttaagg taactcttat ttttaaccgg          60
tgagctccct aggagatctt taattaatac gtagctagcc                                100

<210> SEQ ID NO 59
<211> LENGTH: 79
<212> TYPE: DNA
<213> ORGANISM: Artificial Sequence
<220> FEATURE:
<223> OTHER INFORMATION: Specific primer

<400> SEQUENCE: 59
ctagctagcg gcgtaaaaag cttagcgggc ggcttcgtat atacggcggc tgacatccaa          60
cgtaatgtcg tgattttcg                                                    79

<210> SEQ ID NO 60
<211> LENGTH: 43
<212> TYPE: DNA
<213> ORGANISM: Artificial Sequence
<220> FEATURE:
<223> OTHER INFORMATION: Specific primer

<400> SEQUENCE: 60
cgatgcacgt catgaacaac tttaatctgc acaccccaac ccg                         43

<210> SEQ ID NO 61
<211> LENGTH: 29
<212> TYPE: DNA
<213> ORGANISM: Artificial Sequence
<220> FEATURE:
<223> OTHER INFORMATION: Specific primer

<400> SEQUENCE: 61
cgtacgtact gtaggaaagt taactacgg                                         29

<210> SEQ ID NO 62
<211> LENGTH: 29
<212> TYPE: DNA
<213> ORGANISM: Artificial Sequence
<220> FEATURE:
<223> OTHER INFORMATION: Specific primer

<400> SEQUENCE: 62
gaagatcttt acttcagacg gtccgcgag                                         29

<210> SEQ ID NO 63
<211> LENGTH: 28
<212> TYPE: DNA
<213> ORGANISM: Artificial Sequence
<220> FEATURE:
<223> OTHER INFORMATION: Specific primer

<400> SEQUENCE: 63
gacctaggct ctaaaggagc aattatgg                                          28

<210> SEQ ID NO 64
<211> LENGTH: 26
<212> TYPE: DNA
<213> ORGANISM: Artificial Sequence
<220> FEATURE:
<223> OTHER INFORMATION: Specific primer

<400> SEQUENCE: 64
cgagctctta ttcccactct tgcagg                                            26

<210> SEQ ID NO 65
<211> LENGTH: 30
<212> TYPE: DNA
<213> ORGANISM: Artificial Sequence
<220> FEATURE:
<223> OTHER INFORMATION: PCR primer

<400> SEQUENCE: 65
catgccatgg ctatccctgc atttggttta                                        30

<210> SEQ ID NO 66
<211> LENGTH: 30
<212> TYPE: DNA

```
<213> ORGANISM: Artificial Sequence
<220> FEATURE:
<223> OTHER INFORMATION: PCR primer

<400> SEQUENCE: 66
ctagctagct taatcccatt caggagccag                              30

<210> SEQ ID NO 67
<211> LENGTH: 31
<212> TYPE: DNA
<213> ORGANISM: Artificial Sequence
<220> FEATURE:
<223> OTHER INFORMATION: PCR primer

<400> SEQUENCE: 67
catgccatgg ctaatccaac cgttattaag c                            31

<210> SEQ ID NO 68
<211> LENGTH: 30
<212> TYPE: DNA
<213> ORGANISM: Artificial Sequence
<220> FEATURE:
<223> OTHER INFORMATION: PCR primer

<400> SEQUENCE: 68
ctagctagct tagccgccga actggtcagg                              30

<210> SEQ ID NO 69
<211> LENGTH: 41
<212> TYPE: DNA
<213> ORGANISM: Artificial Sequence
<220> FEATURE:
<223> OTHER INFORMATION: synthetic promoter

<400> SEQUENCE: 69
gagctgttga cgattaatca tccggctcga ataatgtgtg g                 41

<210> SEQ ID NO 70
<211> LENGTH: 65
<212> TYPE: DNA
<213> ORGANISM: Artificial Sequence
<220> FEATURE:
<223> OTHER INFORMATION: PCR primer

<400> SEQUENCE: 70 cctttattc actaacaaat agctggtgga atatatgtcc aacaatggct cgtcaccgct    60
ggtgc                                                              65

<210> SEQ ID NO 71
<211> LENGTH: 43
<212> TYPE: DNA
<213> ORGANISM: Artificial Sequence
<220> FEATURE:
<223> OTHER INFORMATION: PCR primer

<400> SEQUENCE: 71
aatcgcaagc ttgaatccgg ttatttcttc agttcagcca ggc               43

<210> SEQ ID NO 72
<211> LENGTH: 65
<212> TYPE: DNA
<213> ORGANISM: Artificial Sequence
<220> FEATURE:
<223> OTHER INFORMATION: PCR primer

<400> SEQUENCE: 72
```

```
gcaccagcgg tgacgagcca ttgttggaca tatattccac cagctatttg ttagtgaata      60
aaagg                                                                  65

<210> SEQ ID NO 73
<211> LENGTH: 33
<212> TYPE: DNA
<213> ORGANISM: Artificial Sequence
<220> FEATURE:
<223> OTHER INFORMATION: PCR primer

<400> SEQUENCE: 73
acgtcccggg caagcccaaa ggaagagtga ggc                                   33
```

MICROORGANISMS AND METHODS FOR PRODUCTION OF 1,2-PROPANEDIOL AND ACETOL

CROSS REFERENCE TO RELATED APPLICATIONS

This application is a §371 National Stage Application of PCT/EP2008/053448 filed Mar. 21, 2008, which claims priority to PCT/IB2007/001677 filed Mar. 23, 2007.

BACKGROUND OF THE INVENTION

1. Field of the Invention

The present invention concerns a modified microorganism and its use for the preparation of 1,2-propanediol and/or acetol.

2. Description of Related Art 1,2-propanediol or propylene glycol, a C3 dialcohol, is a widely-used chemical. It is a component of unsaturated polyester resins, liquid detergents, coolants, anti-freeze and de-icing fluids for aircraft. Propylene glycol has been increasingly used since 1993-1994 as a replacement for ethylene derivatives, which are recognised as being more toxic than propylene derivatives.

1,2-propanediol is currently produced by chemical means using a propylene oxide hydration process that consumes large amounts of water. Propylene oxide can be produced by either of two processes, one using epichlorhydrin, and the other hydroperoxide. Both routes use highly toxic substances. In addition, the hydroperoxide route generates by-products such as tert-butanol and 1-phenyl ethanol. For the production of propylene to be profitable, a use must be found for these by-products. The chemical route generally produces racemic 1,2-propanediol, whereas each of the two stereoisomers (R)1,2-propanediol and (S)1,2-propanediol are of interest for certain applications (e.g. chiral starting materials for specialty chemicals and pharmaceutical products).

Acetol or hydroxyacetone (1-hydroxy-2-propanone) is a C3 keto alcohol. This product is used in vat dyeing process in the textile industry as a reducing agent. It can advantageously replace traditional sulphur containing reducing agents in order to reduce the sulphur content in wastewater, harmful for the environment. Acetol is also a starting material for the chemical industry, used for example to make polyols or heterocyclic molecules. It possesses also interesting chelating and solvent properties.

Acetol is currently produced mainly by catalytic oxidation or dehydration of 1,2-propanediol. New processes starting from renewable feedstocks like glycerol are now proposed (see DE4128692 and WO 2005/095536). Currently, the production cost of acetol by chemical processes reduces its industrial applications and markets.

The disadvantages of the chemical processes for the production of 1,2-propanediol and/or acetol make biological synthesis an attractive alternative. Two routes have been characterized for the natural production of these products from sugars by microorganisms.

In the first route 6-deoxy sugars (e.g. L-rhamnose or L-fucose) are cleaved into dihydroxyacetone phosphate and (S)-lactaldehyde, which can be further reduced to (S)-1,2-propanediol (Badia et al, 1985). This route is functional in *E. coli*, but can not yield an economically feasible process due to the elevated cost of the deoxyhexoses.

The second route is the metabolism of common sugars (e.g. glucose or xylose) through the glycolysis pathway followed by the methylglyoxal pathway. Dihydroxyacetone phosphate is converted to methylglyoxal that can be reduced either to lactaldehyde or to acetol. These two compounds can then undergo a second reduction reaction yielding 1,2-propanediol. This route is used by natural producers of (R)-1,2-propanediol, such as *Clostridium sphenoides* and *Thermoanaerobacter thermosaccharolyticum*. *Clostridium sphenoides* has been used to produce 1,2-propanediol at a titer of 1.58 g/l under phosphate limited conditions (Tran Din and Gottschalk, 1985). *Thermoanaerobacter thermosaccharolyticum* has also been investigated for the production of 1,2-propanediol (Cameron and Cooney, 1986, Sanchez-Rivera et al, 1987). The best performances obtained were a titer of 9 g/l and a yield from glucose of 0.2 g/g. However, the improvement of the performances obtained with these organisms is likely to be limited due to the shortage of available genetic tools.

*E. coli* has the genetic capabilities to produce naturally 1,2-propanediol and acetol. The biosynthetic pathway to 1,2-propanediol starts from the glycolysis intermediate dihydroxyacetone phosphate. This metabolic intermediate can be converted to methylglyoxal by methylglyoxal synthase encoded by mgsA gene (Cooper, 1984, Tötemeyer et al, 1998). Methylglyoxal is an extremely toxic electrophile that can react with nucleophilic centres of macromolecules such as DNA, RNA and proteins. It can inhibit bacterial growth and cause cell death at very low concentrations (0.3 to 0.7 mM). For this reason, the existing routes for detoxification of methylglyoxal have been investigated (Ferguson et al, 1998). Three pathways have been identified in bacteria and specifically in *E. coli*:

The first one is the gluthathione dependent glyoxalase I-II system (encoded by gloA and gloB genes) which converts methylglyoxal into D-lactate in two steps.

The second one is the glutathione independent glyoxalase III enzyme which catalyses the conversion of methylglyoxal into D-lactate.

The third system encompasses the degradation of methylglyoxal by methylglyoxal reductases.

This last system is relevant for the production of 1,2-propanediol. Methylglyoxal is a C3 ketoaldehyde, bearing an aldehyde at C1 and a ketone at C2. Theses two positions can be reduced to alcohol, yielding respectively acetol (or hydroxyacetone), a non-chiral molecule and lactaldehyde, a chiral molecule which can exist in L- or D-form (see FIG. 1). These 3 molecules, acetol, L-lactaldehyde and D-lactaldehyde can be subsequently reduced at the other position to yield chiral 1,2-propanediol.

The pathways preferentially used in *E. coli* are not clearly established at this time. A methylglyoxal reductase, using preferentially NADPH as co-factor, was purified and partially characterized in *E. coli* (Saikusa et al, 1987). The product of this reaction was shown to be lactaldehyde. Misra et al (1996) described the purification of two methylglyoxal reductase activities giving the same product acetol. One NADH dependent activity could be an alcohol dehydrogenase activity whereas the NADPH dependent activity could be a non-specific aldehyde reductase. Altaras and Cameron (1999) demonstrated that glycerol dehydrogenase (GldA) encoded by the gldA gene of *E. coli* is active in reducing methylglyoxal to (R)-lactaldehyde, and also in the conversion of acetol into 1,2-propanediol.

The gene yghZ was cloned from *E. coli*, expressed and the protein was characterized (Grant, 2003). It exhibited a high specific activity toward methylglyoxal with NADPH as a co-factor, but the product of the reaction was not characterized. When overexpressed, this gene conferred resistance to methylglyoxal toxicity.

Ko et al (2005) investigated systematically the 9 aldo-keto reductases of *E. coli* as candidates for the conversion of methylglyoxal into acetol. They showed that 4 purified enzymes, YafB, YqhE, YeaE and YghZ were able to convert methylglyoxal to acetol in the presence of NADPH. According to their studies, the methylglyoxal reductases YafB, YeaE and YghZ would be the most relevant for the metabolism of methylglyoxal in vivo in terms of detoxification. Di Luccio et al (2006) showed that the product of the gene ydjG of *E. coli* is active on methylglyoxal with NADH but the characterization of the product of the reaction was not done.

Several investigations for genetic modifications of *E. coli* in order to obtain a 1,2-propanediol producer using simple carbon sources have been done by the group of Cameron (Cameron et al, 1998, Altaras and Cameron, 1999, Altaras and Cameron, 2000) and the group of Bennett (Huang et al, 1999, Berrios-Rivera et al, 2003). These studies rely on the expression of one or several genes coding for enzymatic activities in the pathway from dihydroxyacetone phosphate to 1,2-propanediol. Cameron et al (1998) showed that the overexpression of either the gene coding for rat lens aldose reductase or the gldA gene resulted in the production of less than 0.2 g/l 1,2-propanediol. Improvement of this titer can be obtained by co-expressing two *E. coli* genes, mgsA and gldA. With this combination, a titer of 0.7 g/l 1,2-propanediol can be obtained (Altaras and Cameron, 1999). Further improvement in titers and yield were obtained when expressing a complete 1,2-propanediol pathway in *E. coli* (Altaras and Cameron, 2000). Three genes, mgsA, gldA and fucO, have been overexpressed in a strain lacking the gene coding for lactate dehydrogenase (ldhA). With this combination, the best results obtained by the group of Cameron are production of 1.4 g/l 1,2-propanediol in anaerobic flask culture with a yield of 0.2 g/g of glucose consumed. When extrapolated in anaerobic fed-batch fermenter, the production was 4.5 g/l of 1,2-propanediol with a yield of 0.19 g/g from glucose. Results obtained with the same approach but with lower titers and yields are also described in U.S. Pat. No. 6,087,140, U.S. Pat. No. 6,303,352 and WO 98/37204. The group of Bennett also used an *E. coli* host strain lacking ldhA for the overexpression of the mgs gene from *Clostridium acetobutylicum* and the gldA gene from *E. coli*. Flask cultures under anaerobic conditions gave a titer of 1.3 g/l and a yield of 0.12 g/g whereas microaerobic cultures gave a titer of 1.4 g/l with a yield of 0.13 g/g.

At this stage, all these results are not better than those obtained with the species T thermosaccharolyticum.

Up to now, the use of endogeneous activities from microorganisms, and in particular from *E. coli*, converting methylglyoxal to acetol has not been described.

BRIEF DESCRIPTION OF THE INVENTION

The present invention concerns a modified microorganism with an increased methylglyoxal reductase activity and its use for the preparation of 1,2-propanediol and/or acetol. The methylglyoxal reductase enzyme is the product of a gene from microorganisms. The increase of the methylglyoxal reductase activity is obtained by overexpressing one or more genes involved in the conversion of methylglyoxal to acetol, preferably selected among yqhD, yafB, ycdW, yqhE, yeaE, yghZ, yajO, tas, ydjG and ydbC.

In another aspect of the invention, the methylglyoxal synthase activity is also increased by overexpressing the mgsA gene.

In a further aspect of the invention, the Entner-Doudoroff pathway is eliminated by deleting either the edd or eda gene or both. Furthermore, the synthesis of unwanted by-products is attenuated by attenuating the expression of the genes coding for enzymes involved in synthesis of lactate from methylglyoxal (such as gloA, aldA, aldB), lactate from pyruvate (ldhA), formate (pflA, pflB), ethanol (adhE) and acetate (ackA, pta, poxB).

Preferably, half of the glucose is metabolized to dihydroxyacetone phosphate and eventually to 1,2-propanediol and/or acetol by deleting the tpiA gene. Optionally, with an active tpiA gene, the glyceraldehyde 3 phosphate activity is reduced in order to redirect a part of the available glyceraldehyde 3 phosphate toward the synthesis of 1,2-propanediol and/or acetol. In one aspect of the invention, the efficiency of the sugar import is increased, either by using a sugar import independent of phosphoenolpyruvate (PEP) like the one encoded by galP, or by providing more PEP to the sugar-phosphotransferase system. This is obtained by eliminating the pathways consuming PEP like pyruvates kinases (encoded by the pykA and pykF genes) and/or by promoting the synthesis of PEP e.g. by overexpressing the ppsA gene coding for PEP synthase.

Specifically for the production of 1,2-propanediol, the microorganism is optionally modified in order to increase other enzymes converting of dihydroxyacetone phosphate to 1,2-propanediol, like glycerol dehydrogenase (encoded by gldA) and 1,2-propanediol oxidoreductase (encoded by fucO). Additionally, it is valuable for the enzyme converting pyruvate into acetyl-coA to be resistant to high concentrations of NADH found under anaerobic conditions. This can be obtained by a specific mutation in the lpd gene. Finally, in order to spare NADH for the reduction of acetol into 1,2-propanediol, the arcA and the ndh genes can be deleted. The microorganism used for the preparation of 1,2-propanediol is selected among bacteria, yeasts and fungi, but is preferentially either *Escherichia coli* or *Clostridium acetobutylicum*. The present invention provides a process for the production of 1,2-propanediol by cultivating the modified microorganism in an appropriate growth medium containing a simple or a complex carbon source and by recovering and purifying the produced 1,2-propanediol.

Specifically for the production of acetol, the gene coding for glycerol dehydrogenase is attenuated or deleted, preventing the formation of 1,2-propanediol. The microorganism used for the preparation of acetol is selected among bacteria, yeasts and fungi, but is preferentially either *Escherichia coli* or *Klebsiella pneumoniae*. Another object of the present invention is a process for the production of acetol, by cultivating said modified microorganism in an appropriate growth medium containing a simple carbon source and by recovering and purifying the produced acetol.

BRIEF DESCRIPTION OF THE DRAWINGS

The accompanying drawings that are incorporated in and constitute a part of this specification exemplify the invention and together with the description, serve to explain the principles of this invention.

DETAILED DESCRIPTION OF THE INVENTION

Figure 1:
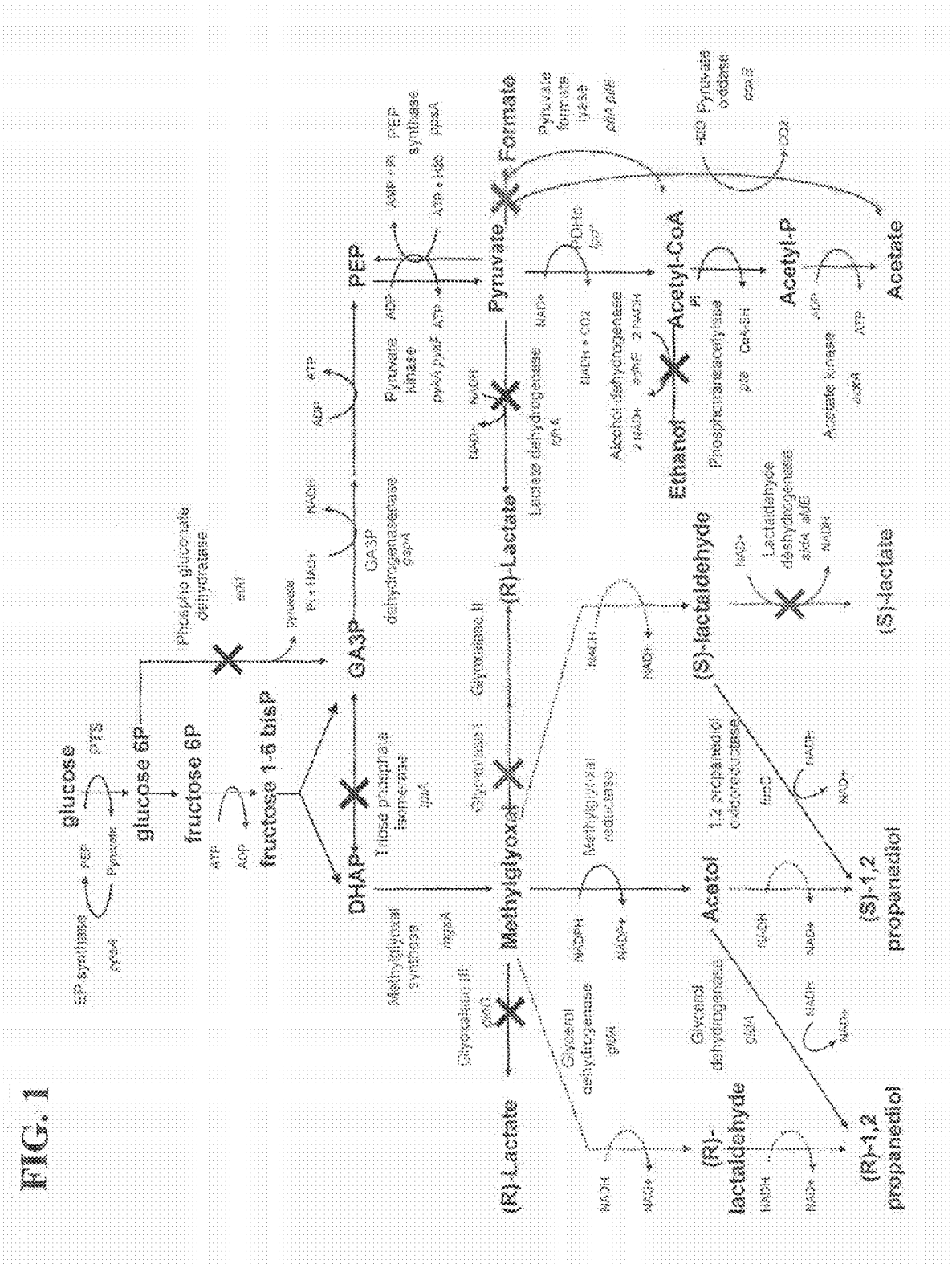
FIG. 1 depicts the genetic engineering of central metabolism in the development of a 1,2-propanediol production system from carbohydrates.

The present invention is related to a modified microorganism useful for the production of 1,2-propanediol and/or acetol from a carbon source, wherein said microorganism is characterized by an increased methyl glyoxal reductase activity, encoded by one or more genes from microorganisms.

As used herein the following terms may be used for interpretation of the claims and specification.

According to the invention the terms 'culture', 'growth' and 'fermentation' are used interchangeably to denote the growth of bacteria on an appropriate growth medium containing a simple carbon source.

The term "modified microorganism" denotes a microorganism such as a bacterium, a yeast or a fungus, that has been modified to increase the methyl glyoxal reductase activity. Such modification includes usual means for transforming microorganisms with genetic elements, including gene replacement or introduction of vectors for the expression of genes involved in methyl glyoxal reduction. It also includes random or directed mutagenesis of the microorganism under usual conditions to induce such mutagenesis. It also includes methods for the evolution of a microorganism such as the evolution method disclosed in WO 2004/076659.

The term "useful for the production" denotes that the microorganism produces the products of interest by fermentation. Fermentation is a classical process that can be performed under aerobic, microaerobic or anaerobic conditions.

The term 'carbon source' according to the present invention denotes any source of carbon that can be used by those skilled in the art to support the normal growth of a microorganism, and which can be hexoses, pentoses, monosaccharides, disaccharides, oligosaccharides, starch or its derivatives, hemicelluloses, glycerol and combinations thereof.

An "increased enzymatic activity" means that the activity is superior to the activity of the wild-type enzyme, as measured in the same microorganism before any modification. The corresponding non-modified microorganism is a microorganism having the same characteristics of the modified microorganism except for the modification of the methyl glyoxal reductase activity. The methyl glyoxal reductase activity can be measured by usual means such as the method disclosed in Misra et al (Molecular and Cellular Biochemistry 156: 117-124 (1996)) or Ko et al (J. Bacteriol. 187: 5782-5789 (2005)).

Advantageously, the methyl glyoxal reductase activity is increased by at least 50%, preferably by at least 100%, compared to the methyl glyoxal reductase activity of the corresponding non-modified microorganism.

Preferentially, the increase of methyl glyoxal reductase activity is obtained by over-expressing at least one gene involved in the methyl glyoxal reduction.

The term "expression" refers to the transcription and translation from a gene sequence leading to the generation of the corresponding protein, product of the gene.

To obtain an overexpression of a gene of interest, the man skilled in the art knows different methods, and for example:

1—Replacement of the native promoter of a gene with a promoter inducing a stronger level of expression of said gene of interest.

A stronger level of expression can be obtained by replacing the native promoter of a gene with a promoter known to induce a strong gene expression in the selected microorganism. Such promoters for *E. coli* are for example the promoters Ptrc, Ptac, Plac, the lambda promoter cI or other promoters known to the expert in the field. For other species of microorganism, those skilled in the art are able to determine the promoters that can be used.

2—Introduction of multiple copies of said gene of interest involved in methyl glyoxal reduction into the microorganism by:

introducing an expression vector carrying and expressing said gene of interest.

introducing additional copies of the gene into the chromosome of the microorganism.

In a specific embodiment of the invention, at least one of the following genes is over-expressed: yqhD, yafB, ydhF, ycdW, yqhE, yeaE, yghZ, yajO, tas, ydjG, and ydbC. Said genes are coding for enzymes able to convert methylglyoxal into acetol. Preferentially the yqhD gene is overexpressed alone or in combination with other genes.

In another embodiment of the invention, the microorganism with an increased methyl glyoxal activity is furthermore modified.

Preferentially, the microorganism according to the invention presents a methyl glyoxal synthase activity that is increased. Advantageously this is obtained by an increase of the expression of the mgsA gene, coding for methylglyoxal synthase involved in the conversion of DHAP into methylglyoxal.

Another way to obtain this increased enzymatic activity is to introduce into the mgsA gene a specific mutation allowing the translation of a gene product presenting a higher activity than the native protein.

Preferentially, in the microorganism according to the invention, at least one gene involved in the Entner-Doudoroff pathway is attenuated. The Entner-Doudoroff pathway provides an alternative way to degrade glucose to glyceraldehyde-3-phosphate and pyruvate besides glycolysis. The attenuation of the Entner-Doudoroff pathway assures that most or at best all glucose is degraded via glycolysis and be utilised for the production of 1,2-propanediol.

Preferably the expression of at least one of the following genes is attenuated: edd, eda.

The term 'attenuation of the activity of an enzyme' refers to a decrease of activity of the enzyme of interest, compared to the observed activity in the same microorganism before any modification. The man skilled in the art knows numerous means to obtain this result, and for example:

Introduction of a mutation into the gene, decreasing the expression level of this gene, or the level of activity of the encoded protein.

Replacement of the natural promoter of the gene by a low strength promoter, resulting in a lower expression.

Use of elements destabilizing the corresponding messenger RNA or the protein.

Deletion of the gene if no expression at all is needed.

The term 'attenuation of the expression of a gene' according to the invention denotes the partial or complete suppression of the expression of a gene, which is then said to be 'attenuated'. This suppression of expression can be either an inhibition of the expression of the gene, a deletion of all or part of the promoter region necessary for the gene expression, or a deletion in the coding region of the gene. Preferentially, the attenuation of a gene is essentially the complete deletion of that gene, which gene can be replaced by a selection marker gene that facilitates the identification, isolation and purification of the strains according to the invention. A gene is inactivated preferentially by the technique of homologous recombination (Datsenko, K. A. & Wanner, B. L. (2000) "One-step inactivation of chromosomal genes in *Escherichia coli* K-12 using PCR products". Proc. Natl. Acad. Sci. USA 97: 6640-6645).

In another embodiment of the invention, the activity of at least one enzyme involved in the conversion of methylglyoxal into lactate is attenuated. The purpose of this attenuation is that the available methylglyoxal is used by the cell machinery essentially for the synthesis of 1,2-propanediol (see FIG. 1). Genes involved in the conversion of methylglyoxal into lactate are in particular:

the gloA gene coding for glyoxalase I, catalysing the synthesis of lactoyl glutathione from methylglyoxal, the aldA and aldB genes coding for a lactaldehyde dehydrogenase (catalysing the synthesis of (S) lactate from (S) lactaldehyde).

One or more of these genes are advantageously attenuated in the microorganism. Preferentially the gene gloA is attenuated or completely deleted.

In the microorganism of the invention, it is preferable that at least one enzyme involved in the synthesis of by-products such as lactate, ethanol and formate is attenuated.

In particular, it is advantageous to attenuate the gene ldhA coding for lactate dehydrogenase catalysing the synthesis of lactate from pyruvate, and the gene adhE coding for alcohol-aldehyde dehydrogenase catalysing the synthesis of ethanol from acetyl-CoA.

Similarly, it is possible to force the micro-organism to use the pyruvate dehydrogenase complex to produce acetyl-CoA $CO_2$ and NADH from pyruvate, instead of acetyl-CoA and formate. This can be achieved by attenuating the genes pflA and pflB coding for pyruvate formate lyase.

In another specific embodiment of the invention, the synthesis of the by-product acetate is prevented by attenuating at least one enzyme involved in its synthesis It is preferable to avoid such acetate synthesis to optimize the production of 1,2-propanediol.

To prevent the production of acetate, advantageously at least one gene selected among ackA, pta and poxB is attenuated These genes all encodes enzymes involved in the different acetate biosynthesis pathways (see FIG. 1).

In a specific embodiment of the invention, the triose phosphate isomerase activity is attenuated. Preferentially, this result is achieved by attenuating the expression of the tpiA gene. The tpiA gene encodes the enzyme 'triose phosphate isomerase', which catalyses the conversion of DHAP into glyceraldehyde 3-phosphate (see FIG. 1). The attenuation of the expression of this gene ensures that half of the glucose metabolized is converted to 1,2-propanediol and/or acetol.

In a specific embodiment of the invention, the glyceraldehyde 3 phosphate dehydrogenase activity is attenuated. The glyceraldehyde 3-phosphate dehydrogenase, also called GAPDH, is one of the key enzymes involved in the glycolytic conversion of glucose to pyruvic acid. The attenuation of the enzyme resulted in the redirection of part of the GA3P toward the synthesis of 1,2-propanediol and:or acetol. The yield of 1,2-propanediol over glucose can then be greater than 1 mole/mole. Advantageously, the activity of the glyceraldehyde 3-phosphate dehydrogenase is about less than 30% of the usual activity of a wild-type GADPH, more preferably less than 10%.

Preferentially, the expression of the gapA gene coding for GAPDH is attenuated.

Preferentially, in the microorganism according to the invention, the efficiency of the sugar import is increased. A strong attenuation of the expression of the gapA gene resulting in a decrease of the carbon flux in the GAPDH reaction by more than 50%, this will result in the synthesis of less than 1 mole of PEP per mole of glucose imported. PEP is required by the sugar-phosphotransferase system (PTS) normally used for the import of simple sugars into the cell, since import is coupled to a phospho-transfer from PEP to glucose yielding glucose-6-phosphate. Thus reducing the amount of PEP will negatively impact on sugar import.

In a specific embodiment of the invention, the sugar might be imported into the microorganism by a sugar import system independent of phosphoenolpyruvate. The galactase-proton symporter encoded by the gene galP that does not involve phosphorylation can be utilized. In this case, the imported glucose has to be phosphorylated by the glucose kinase activity encoded by the glk gene. To promote this pathway, the expression of at least one gene selected among galP and glk is increased. As a result the PTS becomes dispensable, it can be eliminated by attenuating at least one gene selected among ptsH, ptsI or crr.

In another specific embodiment of the invention, the efficiency of the sugar-phosphotransferase system (PTS) is increased by increasing the availability of the metabolite phosphoenopyruvate. Due to the attenuation of the gapA activity and of the lower carbon flux toward pyruvate, the amount of PEP in the modified strain of the invention could be limited, leading to a lower amount of glucose transported into the cell.

Various means exist that may be used to increase the availability of PEP in a strain of microorganism. In particular, a mean is to attenuate the reaction PEP→pyruvate. Preferentially, at least one gene selected among pykA and pykF, coding for the pyruvate kinase enzyme, is attenuated in said strain to obtain this result. Another way to increase the availability of PEP is to favour the reaction pyruvate→PEP, catalysed by the phosphoenolpyruvate synthase by increasing the activity of this enzyme. This enzyme is encoded by the ppsA gene. Therefore, preferentially in the microorganism, the expression of the ppsA gene is preferentially increased. Both modifications can be present in the microorganism simultaneously.

In a specific embodiment of the invention, the modified microorganism is designed to produce mainly 1,2-propanediol. This result is achieved by favouring the conversion of acetol and other precursors (e.g. lactaldehyde) into 1,2-propanediol. This includes:

increasing the glycerol dehydrogenase activity. Preferentially the expression of the gldA gene is increased.

Increasing the 1,2-propanediol oxidoreductase activity, preferably by increasing the expression of the fucO gene.

Especially under anaerobic or microaerobic conditions, it is advantageous that the enzyme that favours the metabolism of pyruvate into acetyl coA (in particular the pyruvate dehydrogenase complex), has low sensitivity to inhibition by NADH. Lower sensitivity is defined with reference to the sensitivity of the wild-type enzyme. Such characteristic can be obtained by a specific mutation in the lpd gene (coding for the sub-unit lipoamide dehydrogenase of the PDC) resulting in the replacement of alanine 55 in the protein sequence of the enzyme by the residue valine.

Under anaerobic or microaerobic conditions, availability of NADH for the reduction of the precursors into 1,2-propanediol is advantageously increased. This is obtained by alleviating the repression on the tricarboxylic acid cycle mediated by the global regulator ArcA (encoded by the arcA gene). NADH concentration in the cell can also be increased by inactivating the NADH dehydrogenase II encoded by the gene ndh. Therefore, preferably, the expression of at least one gene selected among arcA and ndh is attenuated.

Preferentially the microorganism designed to produce mainly 1,2-propanediol is selected among bacteria, yeasts or fungi. More preferentially, the microorganism is selected among Enterobacteriaceae, Bacillaceae, Clostridiaceae, Streptomycetaceae and Corynebacteriaceae. Even more preferentially, the microorganism is either from the species *Escherichia coli* or from the species *Clostridium acetobutylicum*.

In another specific embodiment of the invention, the modified microorganism is designed to produce mainly acetol. Preferably, this result is achieved by attenuating the activity of at least one enzyme involved in the conversion of acetol into 1,2-propanediol. Preferentially, the expression of the gldA gene is attenuated.

Advantageously the microorganism designed to produce mainly acetol is a bacterium, a yeast or a fungus. More preferentially, the microorganism is selected among the species: Enterobacteriaceae, Bacillaceae, Streptomycetaceae and Corynebacteriaceae. Even more preferentially, the microorganism is either from the species *Escherichia coli* or *Klebsiella pneumoniae*.

The invention is also related to a method for preparing 1,2-propanediol, wherein a microorganism according to the invention is grown in an appropriate growth medium containing a carbon source, and the produced 1,2-propanediol is recovered. The production of 1,2-propanediol is performed under aerobic, microaerobic or anaerobic conditions.

In one embodiment, a microorganism of the species *Escherichia coli* is grown in an appropriate growth medium containing a simple carbon source.

In another embodiment, a microorganism of the species *Clostridium acetobutylicum* is grown in an appropriate growth medium containing a simple or a complex carbon source.

Advantageously the recovered 1,2-propanediol is furthermore purified.

The invention is also related to a method for preparing acetol, wherein a microorganism according to the invention is grown in an appropriate growth medium containing a simple carbon source, and the produced acetol is recovered. The production of acetol is performed under aerobic or microaerobic conditions, preferentially under aerobic conditions.

Advantageously, the recovered acetol is furthermore purified.

The culture conditions for the fermentation process can be readily defined by those skilled in the art. In particular, bacteria are fermented at temperatures between 20° C. and 55° C., preferably between 25° C. and 40° C., and preferably at about 35° C. for *C. acetobutylicum* and at about 37° C. for *E. coli* and *K. pneumoniae*.

This process can be carried out either in a batch process, in a fed-batch process or in a continuous process.

'Under aerobic conditions' means that oxygen is provided to the culture by dissolving the gas into the liquid phase. This could be obtained by (1) sparging oxygen containing gas (e.g. air) into the liquid phase or (2) shaking the vessel containing the culture medium in order to transfer the oxygen contained in the head space into the liquid phase. Advantages of the fermentation under aerobic conditions instead of anaerobic conditions is that the presence of oxygen as an electron acceptor improves the capacity of the strain to produce more energy in form of ATP for cellular processes. Therefore the strain has its general metabolism improved.

Micro-aerobic conditions are defined as culture conditions wherein low percentages of oxygen (e.g. using a mixture of gas containing between 0.1 and 10% of oxygen, completed to 100% with nitrogen), is dissolved into the liquid phase.

Anaerobic conditions are defined as culture conditions wherein no oxygen is provided to the culture medium. Strictly anaerobic conditions are obtained by sparging an inert gas like nitrogen into the culture medium to remove traces of other gas. Nitrate can be used as an electron acceptor to improve ATP production by the strain and improve its metabolism.

The term 'appropriate growth medium' according to the invention denotes a medium of known molecular composition adapted to the growth of the micro-organism. For example a mineral culture medium of known set composition adapted to the bacteria used, containing at least one carbon source. In particular, the mineral growth medium for *E. coli* or *K. pneumoniae* can thus be of identical or similar composition to M9 medium (Anderson, 1946, *Proc. Natl. Acad. Sci. USA* 32:120-128), M63 medium (Miller, 1992; A Short Course in Bacterial Genetics: A Laboratory Manual and Handbook for *Escherichia coli* and Related Bacteria, Cold Spring Harbor Laboratory Press, Cold Spring Harbor, N.Y.) or a medium such as that defined by Schaefer et al. (1999, *Anal. Biochem.* 270: 88-96), and in particular the minimum culture medium named MPG described below:

| | |
|---|---|
| $K_2HPO_4$ | 1.4 g/l |
| Nitrilo Triacetic Acid | 0.2 g/l |
| trace element solution* | 10 ml/l |
| $(NH_4)_2SO_4$ | 1 g/l |
| NaCl | 0.2 g/l |
| $NaHCO_3$ | 0.2 g/l |
| $MgSO_4$ | 0.2 g/l |
| glucose | 20 to 100 g/l |
| $NaNO_3$ | 0.424 g/l |
| thiamine | 10 mg/l |
| $FeSO_4, 7H_2O$ | 50 mg/l |
| yeast extract | 4 g/l |

*trace element solution: Citric acid 4.37 g/L, $MnSO_4$ 3 g/L, $CaCl_2$ 1 g/L, $CoCl_2, 2H_2O$ 0.1 g/L, $ZnSO_4, 7H_2O$ 0.10 g/L, $CuSO_4, 5H_2O$ 10 mg/L, $H_3BO_3$ 10 mg/L, $Na_2MoO_4$ 8.31 mg/L.

The pH of the medium is adjusted to 7.4 with sodium hydroxide.

The carbon source used for the culture of *E. coli* or *K. pneumoniae* is preferentially a simple carbon source and can be arabinose, fructose, galactose, glucose, lactose, maltose sucrose or xylose. An especially preferred simple carbon source is glucose.

The growth medium for *C. acetobutylicum* can thus be of identical or similar composition to Clostridial Growth Medium (CGM, Wiesenborn et al., Appl. Environm. Microbiol., 54: 2717-2722) or a mineral growth medium as given by Monot et al. (Appl. Environm. Microbiol., 44: 1318-1324) or Vasconcelos et al. (J. Bacteriol., 176: 1443-1450).

The carbon source used for the culture of *C. acetobutylicum* is either a simple or a complex carbon. The simple carbon source can be arabinose, fructose, galactose, glucose, lactose, maltose sucrose or xylose. An especially preferred simple carbon source is glucose. The complex carbon source can be starch or hemicellulose. An especially preferred complex carbon source is starch.

The invention is described above, below and in the Examples with respect to *E. coli*. Thus the genes that can be attenuated, deleted or over-expressed for the initial and evolved strains according to the invention are defined mainly using the denomination of the genes from *E. coli*. However, this designation has a more general meaning according to the invention, and covers the corresponding genes in other microorganisms. Using the GenBank references of the genes from *E. coli*, those skilled in the art can determine equivalent genes in other organisms than *E. coli*.

The means of identification of the homologous sequences and their percentage homologies are well-known to those skilled in the art, and include in particular the BLAST programmes that can be used on the website www.ncbi.nlm.nih.gov/BLAST with the default parameters indicated on that website. The sequences obtained can be exploited (aligned) using for example the programmes CLUSTALW www.ebi.ac.uk/clustalw), with the default parameters indicated on these websites.

The PFAM database (protein families database of alignments and hidden Markov models www.sanger.ac.uk/Software/Pfam/) is a large collection of alignments of protein sequences. Each PFAM makes it possible to visualise multiple alignments, view protein domains, evaluate distributions among organisms, gain access to other databases and visualise known protein structures.

COGs (clusters of orthologous groups of proteins www.ncbi.nlm.nih.gov/COG) are obtained by comparing protein sequences derived from 66 fully sequenced unicellular genomes representing 44 major phylogenetic lines. Each COG is defined from at least three lines, making it possible to identify ancient conserved domains.

REFERENCES IN ORDER OF THE CITATION IN THE TEXT

1. Badia J, Ros J, Aguilar J (1985), *J. Bacteriol.* 161: 435-437.
2. Tran Din K and Gottschalk G (1985), *Arch. Microbiol.* 142: 87-92
3. Cameron D C and Cooney C L (1986), *Bio/Technology,* 4: 651-654
4. Sanchez-Rivera F, Cameron D C, Cooney C L (1987), *Biotechnol. Lett.* 9: 449-454
5. Cooper R A (1984), *Annu. Rev. Microbiol.* 38: 49-68
6. Tötemeyer S, Booth N A, Nichols W W, Dunbar B, Booth I R (1998), *Mol. Microbiol.* 27: 553-562
7. Ferguson G P, Tötemeyer S, MacLean M J, Booth I R (1998), *Arch. Microbiol.* 170: 209-218
8. Saikusa T, Rhee H I, Watanabe K, Murata K, Kimura A (1987), *Agric. Biol. Chem.* 51: 1893-1899
9. Misra K, Banerjee A B, Ray S, Ray M (1996), *Mol. Cell. Biochem.* 156: 117-124
10. Altaras N E and Cameron D C (1999), *Appl. Environ. Microbiol.* 65: 1180-1185
11. Grant A W, Steel G, Waugh H, Ellis E M (2003), *FEMS Microbiol. Lett.* 218: 93-99
12. Di Luccio E, Elling R A, Wilson D K (2006), *Biochem. J.* 400: 105-114
13. Ko J, Kim I, Yoo S, Min B, Kim K, Park C (2005), *J. Bacteriol.* 187: 5782-5789
14. Cameron D C, Altaras N E, Hoffman M L, Shaw A J (1998), *Biotechnol. Prog.* 14: 116-125
15. Altaras N E and Cameron D C (2000), *Biotechnol. Prog.* 16: 940-946
16. Huang K, Rudolph F B, Bennett G N (1999), *Appl. Environ. Microbiol.* 65: 3244-3247
17. Berrios-Rivera S J, San K Y, Bennett G N (2003), *J. Ind. Microbiol. Biotechnol.* 30: 34-40
18. Datsenko K A and Wanner B L (2000), *Proc. Natl. Acad. Sci. USA* 97: 6640-6645
19. Anderson E H (1946), *Proc. Natl. Acad. Sci. USA* 32:120-128
20. Miller (1992), A Short Course in Bacterial Genetics: A Laboratory Manual and Handbook for *Escherichia coli* and Related Bacteria, Cold Spring Harbor Laboratory Press, Cold Spring Harbor, N.Y.
21. Schaefer U, Boos W, Takors R, Weuster-Botz D (1999), *Anal. Biochem.* 270: 88-96
22. Wiesenborn D P, Rudolph R B, Papoutsakis E T (1987), *Appl. Environ. Microbiol.,* 54: 2717-2722
23. Monot F, Martin J R, Petitdemange H, Gay R (1982), *Appl. Environ. Microbiol.* 44: 1318-1324
24. Vasconcelos I, Girbal L, Soucaille P (1994), *J. Bacteriol.* 176: 1443-1450

EXAMPLES

Example 1

Extraction, Purification and Identification of Enzymes Involved in the Reduction of Methylglyoxal in the Strain *E. coli* MG1655 lpd*, ΔtpiA, ΔpflAB, ΔadhE, ldhA::km, ΔgloA, ΔaldA, ΔaldB, Δedd Cultivated in Chemostat a) Purification Process of the NADH- or NADPH-Dependent Enzymes Involved in the Reduction Methylglyoxal:

The overall purification process designed to purify the NADH- or NADPH-dependent enzymes involved in the reduction of methyl is composed of five steps. At each step, the target enzymes were detected by enzyme activity assays. Two enzyme activities were measured: 1) NADPH-dependent methylglyoxal reduction, 2) NADH-dependent methylglyoxal reduction.

1) Microbial biomass was collected from chemostat cultures of the *E. coli* MG1655 lpd* ΔtpiA, ΔpflAB, ΔadhE, ldhA::km, ΔgloA, ΔaldA, ΔaldB, Δedd (for the construction of the strain see WO 2005/073364) carried out either under strictly anaerobic or under microaerobic conditions.

2) The cells were harvested by centrifugation, washed twice with 50 mM HEPES buffer pH 7.5 with 5 mM DTT, resuspended in the same buffer before storage at −20° C.

3) The cells were disrupted by sonication (at 0° C., under anaerobic conditions, in four cycles of 30 s with 2 minutes intervals between each cycle in the presence of protease inhibitors). Cells debris were eliminated by centrifugation and nucleic acids presented in cell homogenate were precipitated by a streptomycin sulphate treatment or hydrolyzed by an enzymatic treatment (benzonase) (table I).

TABLE 1

Influence of benzonase or streptomycin sulphate (bold) treatments of the cell homogenate on enzyme activities involved in methylglyoxal reduction:

| Evaluated activities | Specific activity U/mg | | Total enzyme activity U | |
|---|---|---|---|---|
| NADPH dependent methyl glyoxal reduction | 0.13 | 0.043 | 0.095 | 0.120 |
| NADH dependent methyl glyoxal reduction | 0.285 | 0.149 | 0.209 | 0.408 |

According to table 1, the streptomycin sulphate treatment is more efficient leading to a higher specific activity. It allows to remove the contaminants (nucleic acids and undesirable proteins) while maintaining the biological activities of enzyme of interest.

4) The streptomycin sulphate treated cell homogenate was centrifuged and applied to an anion exchange chromatographic column (Ressource Q, Amersham Bioscience) connected to a AKTA purifier system and equilibrated with 50 mM HEPES buffer with 5 mM DTT. The protein separation was done at pH 7 or 7.5 or 8. Proteins were eluted by a continuous KCl gradient (2%) and collected as separate fractions.

5) The elution fractions containing enzyme activities were pooled and applied to a hydrophobic interaction chromatography column (Hitrap phenyl sepharose, Amersham Biosciences) equilibrated with 50 mM HEPES buffer with 5 mM DTT.

A final step of gel permeation chromatography may be added if needed.

Figure 2:
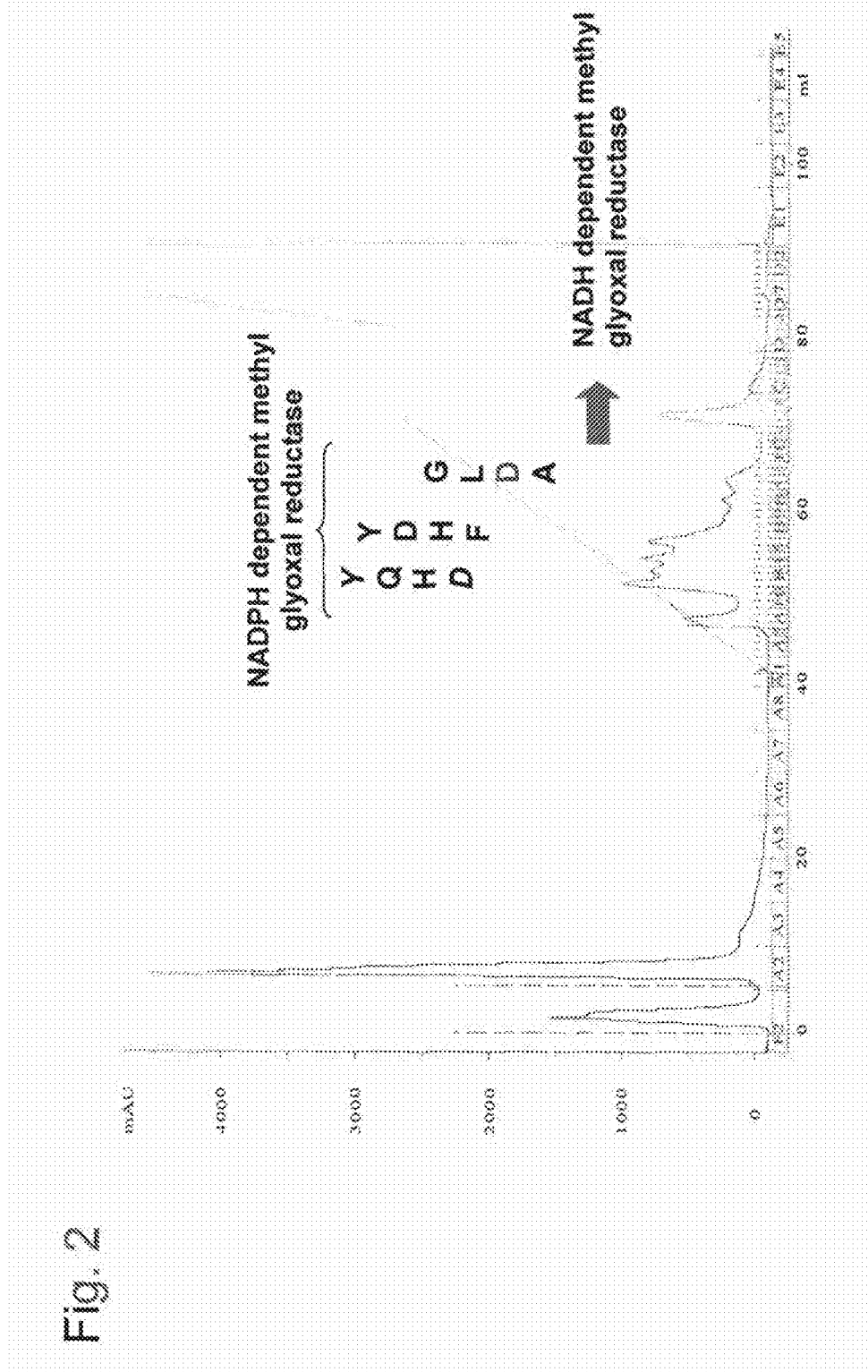
FIG. 2 shows the elution profile of three proteins YQHD, YDHF and GLDA on an anion exchange chromatography column at pH 7.

Yields and purification factor were determined after each step. After the last step of purification, the remaining proteins in the active fractions were separated on a SDS-polyacrylamide gel. The protein of interest was identified by correlating the activity of the fraction with the size of the spots. The protein spot was excised, washed and digested with a specific protease (trypsin digestion) and subjected to mass spectrometry (LC-MS/MS and MALDI) to be identified.

b) Identification of Enzymes Involved in Methylglyoxal Reduction in *E. coli* MG1655 lpd*, ΔtpiA, ΔpflAB, ΔadhE, ldhA::km, ΔgloA, ΔaldA, ΔaldB, Δedd Grown Under Anaerobic Conditions:

The purification process using an anion exchange chromatography at pH 7 followed by a hydrophobic interaction chromatography resulted in the identification of two NADPH dependent enzymes that reduce the methylglyoxal: YQHD (42 KDa) encoded by the yqhD gene and YDHF (33 KDa) encoded by the ydhF gene (FIG. 2). A third enzyme was found (the glycerol dehydrogenase encoded by the gldA gene) to be active in the NADH and NADPH dependent reduction of methylglyoxal.

When the anion exchange chromatography was carried out at pH 8 and followed by a hydrophobic interaction chromatography and a final step of gel permeation chromatography, another NADPH dependent enzyme that reduce the methyl glyoxal was identified: the 2,5-diketo-D-gluconate reductase B (29 KDa) encoded by the dkgB (yafB) gene.

c) Identification of Enzymes Involved in Methylglyoxal Reduction in *E. coli* MG1655 lpd*, ΔtpiA, ΔpflAB, ΔadhE, ldhA::km, ΔgloA, ΔaldA, ΔaldB, Δedd grown under microaerobic conditions:

The purification process designed using an anion exchange chromatography at pH 7.5 resulted in the identification of a 36 KDa protein called YCDW encoded by the ycdW gene catalyzing the NADPH dependent reduction of methylglyoxal.

When the anion exchange chromatography was done at pH 7.5 followed by a hydrophobic interaction chromatography, two others NADPH dependent enzymes catalyzing the reduction of methylglyoxal were identified: YQHD (42 KDa) encoded by the yqhD gene (already purified from cells grown under anaerobic conditions) and the 2,5-diketo-D-gluconate reductase A (31 KDa) encoded by the dkgA (yqhE) gene.

Example 2

Introduction of the Deletions ΔyqhD, ΔyafB, ΔydhF and ΔycdW in Strain *E. coli* MG1655 lpd*, ΔtpiA, ΔpflAB, ΔadhE, ΔldhA::cm, ΔgloA, ΔaldA, ΔaldB, Δedd to Assess the Involvement of the Genes in Methylglyoxal Reduction a) Construction of a Modified Strain *E. coli* MG1655 lpd*, ΔtpiA, ΔpflAB, ΔadhE, ldhA::Km, ΔgloA, ΔaldA, ΔaldB, Δedd The chloramphenicol resistance cassette was eliminated in the strain *E. coli* MG1655 lpd*, ΔtpiA, ΔpflAB, ΔadhE, ldhA::km, ΔgloA, ΔaldA, ΔaldB, Δedd::cm according to protocol 1.

Protocol 1: Elimination of Resistance Cassettes

The chloramphenicol and/or kanamycin resistance cassettes were eliminated according to the following technique. The plasmid pCP20 carrying the FLP recombinase acting at the FRT sites of the chloramphenicol and/or kanamycin resistance cassettes was introduced into the strain by electroporation. After serial culture at 42° C., the loss of the antibiotic resistance cassettes was checked by PCR analysis with the oligonucleotides given in Table 2.

The presence of the modifications previously built in the strain was checked using the oligonucleotides given in Table 2.

The strain obtained was named *E. coli* MG1655 lpd*, ΔtpiA, ΔpflAB, ΔadhE, ldhA::km, ΔgloA, ΔaldA, ΔaldB, Δedd.

TABLE 2

Oligonucleotides used for checking the insertion of a resistance cassette or the loss of a resistance cassette

| Region name | Names of oligos | SEQ ID | Homology with chromosomal region |
|---|---|---|---|
| tpiA gene (deletion) | cdh | N° 1 | See WO2005073364 |
|  | YIIQ | N° 2 |  |
| pflAB gene | pflABF | N° 3 | See WO2005073364 |
|  | pflABR | N° 4 |  |
| adhE gene | ychGf | N° 5 | See WO2005073364 |
|  | adhECr | N° 6 |  |
| ldhA gene (cassette insertion) | hsIJC | N° 7 | See WO2005073364 |
|  | ldhAC2 | N° 8 |  |
| gloA gene | NemACd | N° 9 | See WO2005073364 |
|  | Rnt Cr | N° 10 |  |
| aldA gene | Ydc F C f | N° 11 | See WO2005073364 |
|  | gapCCr | N° 12 |  |
| aldB gene | aldB C f | N° 13 | See WO2005073364 |
|  | YiaYCr | N° 14 |  |
| edd gene | Eda d | N° 15 | See WO2005073364 |
|  | Zwf r | N° 16 |  |
| ldhA gene (deletion) | ldhAF | N° 17 | 1439724 to 1439743 |
|  | ldhAR | N° 18 | 1441029 to 1441007 |
| yqhD gene | yqhDF | N° 19 | 3153060 to 3153092 |
|  | yqhDR | N° 20 | 3154817 to 3154789 |
| yafB gene | yafBF | N° 21 | 228785 to 228804 |
|  | yafBR | N° 22 | 230296 to 230276 |
| ydhF gene | ydhFF | N° 23 | 1722394 to 1722423 |
|  | ydhFR | N° 24 | 1723920 to 1723890 |
| ycdW gene | ycdWF | N° 25 | 1096789 to 1096809 |
|  | ycdWR | N° 26 | 1098297 to 1098277 |
| gapA promoter (Ptrc16-gapA) | yeaAF | N° 27 | 1860259-1860287 |
|  | gapAR | N° 28 | 1861068-1861040 |
| edd and eda genes | eddF | N° 29 | 1932996-1932968 |
|  | edaR | N° 30 | 1929754-1929777 |
| pykA gene | pykAF | N° 31 | 1935338 to 1935360 |
|  | pykAR | N° 32 | 1937425 to 1937401 |
| pykF gene | pykFF | N° 33 | 1753371 to 1753392 |
|  | pykFR | N° 34 | 1755518 to 1755495 | b) Construction of a Modified Strain *E. coli* MG1655 lpd*, ΔtpiA, ΔpflAB, ΔadhE, ΔldhA::cm, ΔgloA, ΔaldA, ΔaldB, Δedd In order to eliminate the kanamycin resistance cassette and to inactivate the ldhA gene, the chloramphenicol resistance cassette was inserting into the ldhA gene deleting most of the gene concerned according to Protocol 2.

Protocol 2: Introduction of a PCR Product for Recombination and Selection of the Recombinants The oligonucleotides chosen and given in Table 3 for replacement of a gene or an intergenic region were used to amplify either the chloramphenicol resistance cassette from the plasmid pKD3 or the kanamycin resistance cassette from the plasmid pKD4 (Datsenko, K. A. & Wanner, B. L. (2000)). The PCR product obtained was then introduced by electroporation into the recipient strain bearing the plasmid pKD46 in which the system λ Red (γβ, exo) expressed greatly favours homologous recombination. The antibiotic-resistant transformants were then selected and the insertion of the resistance cassette was checked by PCR analysis with the appropriate oligonucleotides given in Table 2.

The other modifications of the strain were checked with the oligonucleotides given in Table 2.

The resulting strain was named E. coli MG1655 lpd*, ΔldhA::cmΔtpiA, ΔpflAB, ΔadhE, ΔgloA, ΔaldA, ΔaldB, Δedd.

TABLE 3

Oligonucleotides used for replacement of a chromosomal region by recombination with a PCR product in the strain E. coli MG1655

| Region name | Names of oligos | SEQ ID | Homology with chromosomal region |
|---|---|---|---|
| ldhA gene | DldhAF | N° 35 | 1440865-1440786 |
| | DldhAR | N° 36 | 1439878-1439958 |
| yqhD gene | DyqhDF | N° 37 | 3153369-3153448 |
| | DyqhDR | N° 38 | 3154532-3154452 |
| yafB gene | DyafBF | N° 39 | 229167-229245 |
| | DyafBR | N° 40 | 229966-229887 |
| ydhF gene | DydhFF | N° 41 | 1722760-1722840 |
| | DydhFR | N° 42 | 1723656-1723576 |
| ycdW gene | DycdWF | N° 43 | 1097074-1097150 |
| | DycdWR | N° 44 | 1098047-1097969 |
| gapA promoter (Ptrc16-gapA) | Ptrc-gapAF | N° 45 | 1860478-1860536 |
| | Ptrc-gapAR | N° 46 | 1860762-1860800 |
| edd and eda genes | DeddF | N° 47 | 1932582-1932501 |
| | DedaR | N° 48 | 1930144-1930223 |
| gloA gene | GLOAD f | N° 49 | 1725861-1725940 |
| | GLOA D R | N° 50 | 1726268-1726189 |
| pykA gene | DpykAF | N° 51 | 1935756-1935836 |
| | DpykAR | N° 52 | 1937055-1937135 |
| pykF gene | DpykFF | N° 53 | 1753689-1753766 |
| | DpykFR | N° 54 | 1755129-1755051 | c) Construction of a Modified Strain E. coli MG1655 lpd*, ΔtpiA, ΔpflAB, ΔadhE, ΔldhA, ΔgloA, ΔaldA, ΔaldB, Δedd, ΔyqhD The gene yqhD was inactivated in the strain E. coli MG1655 lpd*, ΔtpiA, ΔpflAB, ΔadhE, ΔldhA::cm, ΔgloA, ΔaldA, ΔaldB, Δedd by inserting a kanamycin antibiotic resistance cassette and deleting most of the gene concerned using the technique described in Protocol 2 with the oligonucleotides given in Table 3.

The resulting strain was named E. coli MG1655 lpd*, ΔtpiA, ΔpflAB, ΔadhE, ΔldhA::cm, ΔgloA, ΔaldA, ΔaldB, Δedd, ΔyqhD::km.

The other modifications of the strain were checked with the oligonucleotides given in Table 2.

The chloramphenicol and kanamycin resistance cassettes were then eliminated according to Protocol 1.

The strain obtained was named E. coli MG1655 lpd*, ΔtpiA, ΔpflAB, ΔadhE, ΔldhA, ΔgloA, ΔaldA, ΔaldB, Δedd, ΔyqhD.

d) Construction of a Modified Strain E. coli MG1655 lpd*, ΔtpiA, ΔpflAB, ΔadhE, ΔldhA, ΔgloA, ΔaldA, ΔaldB. Δedd, ΔyafB The gene yafB was inactivated in strain E. coli MG1655 by inserting a kanamycin antibiotic resistance cassette and deleting most of the gene concerned using the technique described in Protocol 2 with the oligonucleotides given in Table 3. The resulting strain was named E. coli MG1655 ΔyafB::km.

The deletion of the gene yafB by replacement of the gene by a kanamycin resistance cassette in the strain E. coli MG1655 lpd*, ΔtpiA, ΔpflAB, ΔadhE, ΔldhA::cm, ΔgloA, ΔaldA, ΔaldB, Δedd was performed by the technique of transduction with phage P1.

Protocol 3: Transduction with Phage P1 for Deletion of a Gene

The deletion of the chosen gene by replacement of the gene by a resistance cassette (kanamycin or chloramphenicol) in the recipient E. coli strain was performed by the technique of transduction with phage P1. The protocol was in two steps, (i) the preparation of the phage lysate on the strain MG1655 with a single gene deleted and (ii) the transduction of the recipient strain by this phage lysate.

Preparation of the Phage Lysate

Seeding with 100 μl of an overnight culture of the strain MG1655 with a single gene deleted of 10 ml of LB+Cm 30 μg/ml+glucose 0.2%+CaCl$_2$ 5 mM.

Incubation for 30 min at 37° C. with shaking.

Addition of 100 μl of phage lysate P1 prepared on the wild type strain MG1655 (approx. 1×10$^9$ phage/ml).

Shaking at 37° C. for 3 hours until all cells were lysed.

Addition of 200 ml of chloroform, and vortexing.

Centrifugation for 10 min at 4500 g to eliminate cell debris.

Transfer of supernatant in a sterile tube and addition of 200 μl of chloroform.

Storage of the lysate at 4° C.

Transduction

Centrifugation for 10 min at 1500 g of 5 ml of an overnight culture of the E. coli recipient strain in LB medium.

Suspension of the cell pellet in 2.5 ml of MgSO$_4$ 10 mM, CaCl$_2$ 5 mM.

Control tubes: 100 μl cells
  100 μl phages P1 of the strain MG1655 with a single gene deleted.

Tube test: 100 μl of cells+100 μl phages P1 of strain MG1655 with a single gene deleted.

Incubation for 30 min at 30° C. without shaking.

Addition of 100 ml sodium citrate 1 M in each tube, and vortexing.

Addition of 1 ml of LB.

Incubation for 1 hour at 37° C. with shaking.

Plating on dishes LB+Cm 30 μg/ml after centrifugation of tubes for 3 min at 7000 rpm.

Incubation at 37° C. overnight.

The antibiotic-resistant transformants were then selected and the insertion of the deletion was checked by a PCR analysis with the appropriate oligonucleotides given in Table 1.

The other modifications of the strain were checked with the oligonucleotides given in Table 2.

The resulting strain was named E. coli MG1655 lpd*, ΔtpiA, ΔpflAB, ΔadhE, ΔldhA::cm, ΔgloA, ΔaldA, ΔaldB, Δedd, ΔyafB::km.

The chloramphenicol and kanamycin resistance cassettes were then eliminated according to Protocol 1.

The strain obtained was named E. coli MG1655 lpd*, ΔtpiA, ΔpflAB, ΔadhE, ΔldhA, ΔgloA, ΔaldA, ΔaldB, Δedd, ΔyafB.

e) Construction of a Modified Strain E. coli MG1655 lpd*, ΔtpiA, ΔpflAB, ΔadhE, ΔldhA, ΔgloA, ΔaldA, ΔaldB, Δedd, ΔydhF The gene ydhF was inactivated in the strain E. coli MG1655 lpd*, ΔtpiA, ΔpflAB, ΔadhE, ΔldhA::cm, ΔgloA, ΔaldA, ΔaldB, Δedd by inserting a kanamycin antibiotic resistance cassette and deleting most of the gene concerned using the technique described in Protocol 2 with the oligonucleotides given in Table 3. The resulting strain was named E. coli MG1655 lpd*, ΔtpiA, ΔpflAB, ΔadhE, ΔldhA::cm, ΔgloA, ΔaldA, ΔaldB, Δedd, ΔydhF::km.

The other modifications of the strain were checked with the oligonucleotides given in Table 2.

The chloramphenicol and kanamycin resistance cassettes were then eliminated according to Protocol 1.

The strain obtained was named E. coli MG1655 lpd*, ΔtpiA, ΔpflAB, ΔadhE, ΔldhA, ΔgloA, ΔaldA, ΔaldB, Δedd, ΔydhF.

f) Construction of a Modified Strain E. coli MG1655 lpd*, ΔtpiA, ΔpflAB, ΔadhE, ΔldhA, ΔgloA, ΔaldA, ΔaldB, Δedd, ΔycdW The gene ycdW was inactivated in strain E. coli MG1655 by inserting a kanamycin antibiotic resistance cassette and deleting most of the gene concerned using the technique described in Protocol 2 with the oligonucleotides given in Table 3. The resulting strain was named E. coli MG1655 ΔycdW::km.

The deletion of the gene ycdW by replacement of the gene by a kanamycin resistance cassette in the strain E. coli MG1655 lpd*, ΔtpiA, ΔpflAB, ΔadhE, ΔldhA::cm, ΔgloA, ΔaldA, ΔaldB, Δedd was performed by the technique of transduction with phage P1 described in Protocol 3.

The lysate of phage P1 was obtained on the strain MG1655 ΔycdW::km, and the transduction of the strain E. coli MG1655 lpd*, ΔtpiA, ΔpflAB, ΔadhE, ΔldhA::cm, ΔgloA, ΔaldA, ΔaldB, Δedd was carried out using this phage lysate.

The resulting strain was named E. coli MG1655 lpd*, ΔtpiA, ΔpflAB, ΔadhE, ΔldhA::cm, ΔgloA, ΔaldA, ΔaldB, Δedd, ΔycdW::km.

The other modifications of the strain were checked with the oligonucleotides given in Table 2.

The chloramphenicol and kanamycin resistance cassettes were then eliminated according to Protocol 1.

The strain obtained was named E. coli MG1655 lpd*, ΔtpiA, ΔpflAB, ΔadhE, ΔldhA, ΔgloA, ΔaldA, ΔaldB, Δedd, ΔycdW.

f) Culture of the Strains Bearing the Deletions in the Genes Coding for the Identified Methylglyoxal Reductases The four strains bearing the deletions ΔyqhD, ΔyafB, ΔydhF and ΔycdW were cultivated in Erlenmeyer flasks under microaerobic conditions in MPG medium at pH 6.7 and at 37° C.

After 72 h of cultivation, production of acetol and 1,2-propanediol was measured by HPLC in the supernatant of the cultures. The results are given in table 4.

TABLE 4

Production of 1,2-propanediol and acetol in strain bearing deletions in genes coding for methylglyoxal reductases (each value is a mean of two values from two different cultures)

| Product (mM) | ΔydhF strain | ΔycdW strain | ΔyafB strain | ΔyqhD strain | Control strain |
|---|---|---|---|---|---|
| 1,2-propanediol | 10.7 | 16.3 | 8.1 | 0 | 16.7 |
| Acetol | 9.3 | 11.1 | 7.2 | 0 | 11.3 |
| Sum | 20.0 | 27.4 | 15.3 | 0 | 28.0 |

The results showed that all the methylglyoxal reductases identified are involved in the conversion of methylglyoxal into acetol and further into 1,2-propanediol. Deletion of yqhD resulted in a strong growth inhibition possibly due to the accumulation of methylglyoxal. Deletions of yafB and ydhF have also a major impact on the production of acetol and 1,2-propanediol.

Example 3

Construction of Modified Strains of E. coli MG1655 (pME101VB01-yqhD-mgsA-gldA), E. coli MG1655 (pME101VB01-yafB-mgsA-gldA) and E. coli MG1655 (pME101VB01-yqhE-mgsA-gldA)

To increase the production of 1,2-propanediol different combinations of genes were expressed from the plasmid pME101VB01 using the trc promoter.

a) Construction of Plasmid pME101VB01

The plasmid pME101VB01 was derived from plasmid pME101 and harbored a multiple cloning site containing recognition site sequences specific for the rare restriction endonucleases NheI, SnaBI, PacI, BglII, AvrII, SacII and AgeI following by the adc transcription terminator of Clostridium acetobutylicum ATCC824.

For the expression from a low copy vector the plasmid pME101 was constructed as follows. The plasmid pCL1920 (Lerner & Inouye, 1990, NAR 18, 15 p 4631—GenBank AX085428) was PCR amplified using the oligonucleotides PME101F and PME101R and the BstZ17'-XmnI fragment from the vector pTrc99A (Amersham Pharmacia Biotech, Piscataway, N.J.) harboring the lacI gene and the trc promoter was inserted into the amplified vector.

```
PME101F (SEQ ID NO 55):
ccgacagtaagacgggtaagcctg

PME101R (SEQ ID NO 56):
agcttagtaaagccctcgctag
```

A synthetic double-stranded nucleic acid linker comprising the multicloning site and adc transcriptional terminator was used to generate pME101VB01. Two 100 bases oligonucleotides that complement flanked by NcoI or HindIII digested restriction sites were annealed. The 100-base pair product was subcloned into NcoI/HindIII digested plasmid pME101 to generate pME101VB01.

```
pME101VB01 1, consisting of 100 bases
(SEQ ID NO 57):
catgggctagctacgtattaattaaagatctcctagg
gagctcaccggtTAAAAATAAGAGTTACCTTAAATGG
TAACTCTTATTTTTTAggcgcgcca pME101VB01 2, consisting of 100 bases
(SEQ ID NO 58):
agcttggcgcgccTAAAAAAATAAGAGTTACCATTTA
AGGTAACTCTTATTTTTAaccggtgagctccctagga
gatctttaattaatacgtagctagcc
``` with:
- a region (underlined lower-case letters) corresponding to the multicloning site
- a region (upper-case letters) corresponding to the adc transcription terminator (sequence 179847 to 179814) of Clostridium acetobutylicum ATCC 824 pSOL1 (NC_001988).

b) Construction of Plasmids for Expression of Different Combinations of Genes of the Biosynthetic Pathway of 1,2-propanediol (pME101VB01-yqhD-mgsA-gldA, pME101VB01-yafB-mgsA-gldA and pME101VB01-yqhE-mgsA-gldA)

The different genes were PCR amplified from genomic DNA of E. coli MG1655 using the oligonucleotides given in Table 1.

TABLE 5 oligonucleotides used for amplification
of genes of 1,2-propanediol pathway

| Gene name | Names of oligos | SEQ ID | Homology with gene | Restriction sites |
|---|---|---|---|---|
| yqhD | yqhDR2 | N° 59 | 3153369-3153400 | BspHI added |
|  | yqhDF2 | N° 60 | 3154544-3154475 | BspHI removed NheI added |
| mgsA | mgsAF | N° 61 | 1026268-1026248 | SnaBI added |
|  | mgsAR | N° 62 | 1025780-1025800 | BglII added |
| gldA | gldAF | N° 63 | 4136631-4136612 | AvrII added |
|  | gldAR | N° 64 | 4135512-4135530 | SacI added |
| yafB | yafB F2 | N° 65 | 229167-229190 | NcoI added |
|  | yafB R | N° 66 | 229970-229950 | NheI added |
| yqhE | yqhE F | N° 67 | 3154641-3154661 | NcoI added |
|  | yqhE R | N° 68 | 3155464-3155444 | NheI added |

The PCR amplified fragments were cut with the restriction enzymes mentioned in Table 5 and cloned into the restriction sites of the plasmid pME101VB01. The following plasmids were built: pME101VB01-yqhD-mgsA-gldA, pME101VB01-yafB-mgsA-gldA and pME101VB01-yqhE-mgsA-gldA. The plasmids were then introduced into the strain *E. coli* MG1655.

Example 4

Construction of Modified Strains of *E. coli* MG1655 Ptrc16-gapA, Δedd-eda, ΔpykA, ΔpykF (pME101VB01-yqhD-mgsA-gldA), (pJB137-PgapA-ppsA), *E. coli* MG1655 Ptrc16-gapA, Δedd-eda, ΔgloA, ΔpykA, ΔpykF (pME101VB01-yafB-mgsA-gldA), (pJB137-PgapA-ppsA) and *E. coli* MG1655 Ptrc16-gapA, Δedd-eda, ΔgloA, ΔpykA, ΔpykF (pME101VB01-yqhE-mgsA-gldA), (pJB137-PgapA-ppsA) Able to Produce 1,2-propanediol with High Yield The replacement of the natural gapA promoter with the synthetic short Ptrc16 promoter (SEQ ID NO 69: gagctgt-tgacgattaatcatccggctcgaataatgtgtgg) into the strain *E. coli* MG1655 was made by replacing 225 pb of upstream gapA sequence with FRT-CmR-FRT and an engineered promoter using the technique described in Protocol 2 with the oligonucleotides given in Table 3.

The insertion of the resistance cassette was checked by PCR analysis with the oligonucleotides given in Table 2.

The resulting strain was named *E. coli* MG1655 Ptrc16-gapA::cm.

The genes edd-eda were inactivated in strain *E. coli* MG1655 by inserting a kanamycin antibiotic resistance cassette and deleting most of the genes concerned using the technique described in Protocol 2 with the oligonucleotides given in Table 3. The strain obtained was named *E. coli* MG1655 Δedd-eda::km.

This deletion was transferred in strain *E. coli* MG1655 Ptrc16-gapA::cm according to Protocol 3.

The resulting strain was named *E. coli* MG1655 Ptrc16-gapA::cm, Δedd-eda::km.

The antibiotic resistance cassettes were then eliminated according to Protocol 1.

The strain MG1655 ΔgloA::cm was built according to Protocol 2 with the oligonucleotides given in Table 3 and this deletion was transferred in the strain previously built according to Protocol 3. The resulting strain was named *E. coli* MG1655 Ptrc16-gapA, Δedd-eda, ΔgloA::cm.

The gene pykA was inactivated into the previous strain by inserting a kanamycin antibiotic resistance cassette according to Protocol 2 with the oligonucleotides given in Table 3. The resulting strain was named *E. coli* MG1655 Ptrc16-gapA, Δedd-eda, ΔgloA::cm, ΔpykA::km.

The antibiotic resistance cassettes were then eliminated according to Protocol 1.

The gene pykF was inactivated by inserting a chloramphenicol antibiotic resistance cassette according to Protocol 2 with the oligonucleotides given in Table 3. The resulting strain was named *E. coli* MG1655 Ptrc16-gapA, Δedd-eda, ΔgloA, ΔpykA, ΔpykF::cm.

The antibiotic resistance cassette was then eliminated according to Protocol 1.

At each step, the presence of all the deletions previously built was checked using the oligonucleotides given in Table 3.

To increase the production of phosphoenolpyruvate the ppsA gene was expressed from the plasmid pJB137 using the gapA promoter. For the construction of plasmid pJB137-PgapA-ppsA, the gene ppsA was PCR amplified from genomic DNA of *E. coli* MG1655 using the following oligonucleotides:

```
1. gapA-ppsAF, consisting of 65 bases
   (SEQ ID NO 70)
   ccttttattcactaacaaatagctggtggaatatATGTCCAACAAT
   GGCTCGTCACCGCTGGTGC
``` with:

a region (upper-case letters) homologous to the sequence (1785106-1785136) of the gene ppsA (1785136 to 1782758), a reference sequence on the website genolist.pasteur.fr/Colibri/), and a region (lower letters) homologous to the gapA promoter (1860794-1860761).

```
2. ppsAR, consisting of 43 bases
   (SEQ ID NO 71)
   aatcgcaagcttGAATCCGGTTATTTCTTCAGTTCAGCCAGGC
``` with:

a region (upper letters) homologous to the sequence (1782758-1782780) the region of the gene ppsA (1785136 to 1782758)

a restriction site HindIII (underlined letters)

At the same time the gapA promoter region of the *E. coli* gene gapA was amplified using the following oligonucleotides:

```
1. gapA-ppsAR, consisting of 65 bases
   (SEQ ID NO 72)
   GCACCAGCGGTGACGAGCCATTGTTGGACATatattccaccagct
   atttgttagtgaataaaagg
``` with:

a region (upper-case letters) homologous to the sequence (1785106-1785136) of the gene ppsA (1785136 to 1782758), and a region (lower letters) homologous to the gapA promoter (1860794-1860761).

```
2. gapAF, consisting of 33 bases
   (SEQ ID NO 73)
   ACGTCCCGGGcaagcccaaaggaagagtgaggc
``` with:
a region (lower letters) homologous to the gapA promoter (1860639-1860661).
a restriction site SmaI (underlined letters)

Both fragments were subsequently fused using the oligonucleotides ppsAR and gapAF (Horton et al. 1989 Gene 77:61-68). The PCR amplified fragment were cut with the restriction enzymes HindIII and SmaI and cloned into the HindIII/SmaI sites of the vector pJB137 (EMBL Accession number: U75326) giving vector pJB137-PgapA-ppsA.

The different pME101VB01 plasmids and pJB137-PgapA-ppsA were introduced into the strain E. coli MG1655 Ptrc16-gapA, ΔeddA-eda, ΔgloA, ΔpykA, ΔpykF. The strains obtained were named respectively E. coli MG1655 Ptrc16-gapA, Δedd-eda, ΔgloA, ΔpykA, ΔpykF, pME101VB01-yqhD-mgsA-gldA, pJB137-PgapA-ppsA (strain 1), E. coli MG1655 Ptrc16-gapA, Δedd-eda, ΔgloA, ΔpykA, ΔpykF, pME101VB01-yafB-mgsA-gldA, pJB137-PgapA-ppsA (strain 2) and E. coli MG1655 Ptrc16-gapA, Δedd-eda, ΔgloA, ΔpykA, ΔpykF, pME101VB01-yqhE-mgsA-gldA, pJB137-PgapA-ppsA (strain 3).

Example 5

Comparison of the Different Strains for 1,2-propanediol Production Under Aerobic Conditions The strains obtained as described in example 4 (strains 1, 2 and 3) and the control strains (control 1: MG1655 pME101VB01-yqhD-mgsA-gldA, control 2: MG1655 pME101VB01-yafB-mgsA-gldA, control 3: MG1655 pME101VB01-yqhE-mgsA-gldA and control 4: MG1655 Ptrc16-gapA, Δedd-eda, ΔgloA, ΔpykA, ΔpykF) were cultivated in an Erlenmeyer flask assay under aerobic conditions in minimal medium with glucose as carbon source. The culture was carried out at 34° C. or 37° C. and the pH was maintained by buffering the culture medium with MOPS. At the end of the culture, 1,2-propanediol, acetol and residual glucose in the fermentation broth were analysed by HPLC and the yields of 1,2-propanediol over glucose and 1,2-propanediol+acetol over glucose were calculated.

| Strain | 1,2-propanediol titer (g/l) | Acetol titer (g/l) | 1,2-propanediol yield (g/g glucose) | 1,2-propanediol + acetol yield (g/g glucose) |
| --- | --- | --- | --- | --- |
| Control 1 | 0.02 | 0 | 0.004 | 0.004 |
| Control 2 | 0 | 0 | 0 | 0 |
| Control 3 | 0.01 | 0 | 0.002 | 0.002 |
| Control 4 | 0.05 | 0.34 | 0 | 0.04 |
| Strain 1 | 2.25 | 1.40 | 0.14 | 0.23 |
| Strain 2 | 1.64 | 1.31 | 0.10 | 0.18 |
| Strain 3 | 0.77 | 0.47 | 0.06 | 0.10 |

The invention claimed is:

1. A modified microorganism useful for the production of 1,2-propanediol and/or acetol from a carbon source, wherein said microorganism comprises:
   a) increased methyl glyoxal reductase activity obtained by overexpressing at least one of the following genes from *Escherichia coli*: yqhD, yafB, ydhF, ycdW, yqhE, yeaE, yghZ, yajO, tas, ydjG, or ydbC, and
   b) an increased activity of the methyl glyoxal synthase, obtained by an increase of the expression of the mgsA gene from *Escherichia coli*, and
   c) wherein the microorganism belongs to the Enterobacteriaceae species.

2. The microorganism of claim 1, wherein the overexpression is obtained by replacing a native promoter of at least one gene involved in a methyl glyoxal reduction with a promoter inducing a stronger level of expression of said gene.

3. The microorganism of claim 1, wherein the overexpression is obtained by introducing multiple copies of at least one gene involved in methyl glyoxal reduction into the microorganism.

4. The microorganism according to claim 1 wherein the activity of at least one enzyme involved in the conversion of methylglyoxal into lactate is attenuated by attenuating the expression of at least one of the following genes: gloA, aldA, aldB.

5. The microorganism according to claim 1 wherein the activity of at least one enzyme involved in the synthesis of lactate, formate and/or ethanol is attenuated by attenuating the expression of at least one of the following genes: IdhA, pflA, pflB, adhE.

6. The microorganism according to claim 1 wherein the activity of at least one enzyme involved in the synthesis of acetate is attenuated by attenuating the expression of at least one of the following genes: ackA, pta, poxB.

7. The microorganism according to claim 1 wherein the triose phosphate isomerase activity is attenuated by attenuating the expression of the tpiA gene.

8. The microorganism according to claim 1 wherein the glyceraldehyde 3 phosphate dehydrogenase activity is attenuated by attenuating the expression of the gapA gene.

9. The microorganism according to claim 1 wherein a sugar import system independent of phosphoenolpyruvate is used, and the expression of at least one gene selected among galP and glk is increased.

10. The microorganism according to claim 1 wherein the efficiency of the sugar-phosphotransferase system is improved by increasing the availability of the metabolite 'phosphoenolpyruvate,' and wherein the activity of at least one pyruvate kinase is attenuated by attenuating the expression of at least one gene selected among pykA and pykF.

11. The microorganism of claim 10 wherein the phosphoenolpyruvate synthase activity is increased by increasing the expression of the ppsA gene.

12. The microorganism according to claim 1 wherein glycerol dehydrogenase activity is increased by increasing the expression of the gldA gene.

13. The microorganism according to claim 1 wherein 1,2-propanediol oxidoreductase activity is increased by increasing the expression of the fucO gene.

14. The microorganism according to claim 1 wherein the enzyme that favours the metabolism of pyruvate into acetyl-CoA has a lower sensitivity to the inhibition by NADH than the unmodified enzyme because the gene lpd has a point mutation leading to a replacement of alanine 55 by valine.

15. The microorganism according to claim 1 wherein the expression of at least one gene selected among arcA and ndh is attenuated.

16. The microorganism of claim 1 wherein the microorganism is *Escherichia coli*.

17. The microorganism according to claim 1 wherein activity of at least one enzyme involved in conversion of acetol into 1,2-propanediol is attenuated by attenuating the expression of the gldA gene.

18. A method for preparing 1,2-propanediol wherein the microorganism according to claim 1 is grown in an appropriate growth medium comprising a carbon source, and the produced 1,2-propanediol is recovered.

19. The method according to claim 18 wherein the microorganism is from the species *Escherichia coli* and the carbon source is a simple carbon source.

20. The method according to claim 18, wherein the recovered 1,2-propanediol is furthermore purified.

21. A method for preparing acetol wherein a microorganism according to claim 1 is grown in an appropriate growth medium comprising a simple carbon source, and produced acetol is recovered.

22. The method according to claim 21 wherein the recovered acetol is furthermore purified.

23. The modified microorganism useful for the production of 1,2-propanediol and/or acetol from a carbon source according to claim 1, wherein said microorganism comprises:
   increased methyl glyoxal reductase activity obtained by overexpressing at least one of the following genes from *E. coli*: yqhD, yafB, ydhF, ycdW, yqhE, yeaE, yghZ, yajO, tas, ydjG, and ydbC;
   increased expression of a mgsA gene from *E. coli*,
   attenuated expression of at least one of edd, or eda, and
   attenuated expression of at least one of gloA, aldA, or aldB.

24. The modified microorganism according to claim 23 wherein said microorganism is characterized by the overexpression of the gene yqhD.

25. The modified microorganism according to claim 23 wherein said microorganism is characterized by the overexpression of the gene yafB.

26. The modified microorganism according to claim 23 wherein said microorganism is characterized by the overexpression of the gene yqhE.

27. The modified microorganism according to claim 23 wherein said microorganism is characterized by the overexpression of the gene ydhF.

28. The modified microorganism according to claim 23 wherein said microorganism is characterized by the overexpression of the gene ycdW.

29. A method for preparing 1,2-propanediol wherein a microorganism according to claim 23 is grown in an appropriate growth medium comprising a carbon source, and the produced 1,2-propanediol is recovered.

30. A method for preparing acetol wherein a microorganism according to claim 23 is grown in an appropriate growth medium comprising a simple carbon source, and produced acetol is recovered.

31. The microorganism of claim 1, wherein the expression of edd or eda is attenuated.

* * * * *